: (12) United States Patent
Krupnik

(10) Patent No.: US 10,405,734 B2
(45) Date of Patent: Sep. 10, 2019

(54) SYSTEM AND METHOD FOR DISPLAYING AN IMAGE STREAM

(71) Applicant: GIVEN IMAGING LTD., Yoqneam (IL)

(72) Inventor: Hagai Krupnik, Nofit (IL)

(73) Assignee: GIVEN IMAGING LTD., Yoqneam (IL)

( * ) Notice: Subject to any disclaimer, the term of this patent is extended or adjusted under 35 U.S.C. 154(b) by 510 days.

(21) Appl. No.: 14/411,161

(22) PCT Filed: Jun. 27, 2013

(86) PCT No.: PCT/IL2013/050550
§ 371 (c)(1),
(2) Date: Dec. 24, 2014

(87) PCT Pub. No.: WO2014/002096
PCT Pub. Date: Jan. 3, 2014

(65) Prior Publication Data
US 2015/0320299 A1 Nov. 12, 2015

Related U.S. Application Data

(60) Provisional application No. 61/666,142, filed on Jun. 29, 2012.

(51) Int. Cl.
*A61B 1/00* (2006.01)
*A61B 1/04* (2006.01)
(52) U.S. Cl.
CPC ...... *A61B 1/00009* (2013.01); *A61B 1/00016* (2013.01); *A61B 1/00045* (2013.01); *A61B 1/041* (2013.01)
(58) Field of Classification Search
None
See application file for complete search history.

(56) References Cited

U.S. PATENT DOCUMENTS 3,909,792 A 9/1975 Harris et al.
4,278,077 A 7/1981 Mizumoto
(Continued)

FOREIGN PATENT DOCUMENTS

EP 1618832 1/2006
EP 1918870 5/2008
(Continued)

OTHER PUBLICATIONS

European Search Report for EP Patent Application No. 13810537.4, dated May 20, 2015.
(Continued)

*Primary Examiner* — Lindsay J Uhl
(74) *Attorney, Agent, or Firm* — Pearl Cohen Zedek Latzer Baratz LLP

(57) ABSTRACT

Systems and methods for displaying an image stream captured by an in vivo imaging device are presented. A method comprises receiving a stream of image frames captured by the in vivo device, each frame comprising a plurality of pixels. A summarized image presentation comprising summarized data elements may be generated, each summarized data element corresponding to at least one frame from the image stream. Summarized data elements are generated by ordering pixels of one or more image frames according to a first sorting parameter, sampling the ordered pixels according to a predetermined sampling scheme to acquire a subset of ordered pixels; and combining or appending sampled pixels to form a summarized data element. The summarized data elements are combined to form a summarized image presentation.

24 Claims, 9 Drawing Sheets

(56) References Cited

U.S. PATENT DOCUMENTS

| | | | |
|---|---|---|---|
| 4,936,823 | A | 6/1990 | Colvin et al. |
| 5,333,244 | A | 7/1994 | Harashima |
| 5,392,072 | A | 2/1995 | Rodriguez et al. |
| 5,519,828 | A | 5/1996 | Rayner |
| 5,604,531 | A | 2/1997 | Iddan et al. |
| 5,697,384 | A | 12/1997 | Miyawaki et al. |
| 5,970,173 | A | 10/1999 | Lee et al. |
| 5,993,378 | A | 11/1999 | Lemelson |
| 6,097,399 | A | 8/2000 | Bhatt et al. |
| 6,188,403 | B1 | 2/2001 | Sacerdoti et al. |
| 6,222,547 | B1 | 4/2001 | Schwuttke et al. |
| 6,240,312 | B1 | 5/2001 | Alfano et al. |
| 6,428,469 | B1 | 8/2002 | Iddan |
| 6,709,387 | B1 | 3/2004 | Glukhovsky et al. |
| 6,944,316 | B2 | 9/2005 | Glukhovsky et al. |
| 7,009,634 | B2 | 3/2006 | Iddan et al. |
| 7,200,253 | B2 | 4/2007 | Glukhovsky et al. |
| 7,215,338 | B2 | 5/2007 | Horn et al. |
| 7,219,034 | B2 | 5/2007 | McGee et al. |
| 7,505,062 | B2 | 3/2009 | Davidson et al. |
| 7,567,692 | B2 | 7/2009 | Buzaglo et al. |
| 7,694,320 | B1 | 4/2010 | Yeo et al. |
| 7,724,928 | B2 | 5/2010 | Glukhovsky et al. |
| 7,986,337 | B2 | 7/2011 | Davidson et al. |
| 8,763,914 | B2 | 7/2014 | Itay et al. |
| 2002/0171669 | A1 | 5/2002 | Meron |
| 2002/0103417 | A1 | 8/2002 | Gazdzinski |
| 2002/0193669 | A1 | 12/2002 | Glukhovsky |
| 2003/0063130 | A1 | 4/2003 | Barbieri et al. |
| 2003/0077223 | A1 | 4/2003 | Glokhovsky et al. |
| 2003/0167000 | A1 | 9/2003 | Mullick et al. |
| 2003/0208107 | A1 | 11/2003 | Refael |
| 2004/0066398 | A1 | 4/2004 | Dolmier et al. |
| 2004/0184639 | A1 | 9/2004 | Jackson et al. |
| 2004/0196287 | A1 | 10/2004 | Wong et al. |
| 2004/0225223 | A1 | 11/2004 | Honda et al. |
| 2004/0249291 | A1 | 12/2004 | Honda et al. |
| 2005/0075551 | A1 | 4/2005 | Horn et al. |
| 2005/0281446 | A1 | 12/2005 | Glukhovsky et al. |
| 2007/0060798 | A1* | 3/2007 | Krupnik ............ A61B 1/00045 600/300 |
| 2007/0118012 | A1 | 5/2007 | Gilad |
| 2007/0173714 | A1 | 7/2007 | Hirakawa |
| 2007/0268280 | A1* | 11/2007 | Fujita ............... A61B 1/00045 345/204 |
| 2007/0287891 | A1* | 12/2007 | Horn ................ A61B 1/00016 600/300 |
| 2008/0086028 | A1* | 4/2008 | Matsui .............. A61B 1/0005 600/109 |
| 2008/0143826 | A1 | 6/2008 | Shibasaki |
| 2009/0003732 | A1 | 1/2009 | Oda |
| 2009/0027486 | A1* | 1/2009 | Hirakawa ......... A61B 1/00009 348/45 |
| 2009/0131746 | A1* | 5/2009 | Seo ................... A61B 1/00045 600/101 |
| 2009/0284589 | A1 | 11/2009 | Radeva et al. |
| 2010/0158330 | A1 | 6/2010 | Guissin et al. |
| 2010/0182412 | A1* | 7/2010 | Taniguchi .............. A61B 1/041 348/65 |
| 2011/0044515 | A1 | 2/2011 | Spyridonos et al. |
| 2011/0164126 | A1* | 7/2011 | Ambor ................ A61B 1/0005 348/65 |
| 2011/0213203 | A1 | 9/2011 | Minai et al. |
| 2011/0249952 | A1* | 10/2011 | Taniguchi .......... A61B 1/00009 386/230 |
| 2012/0113239 | A1 | 5/2012 | Krupnik et al. |
| 2012/0162401 | A1* | 6/2012 | Melder ................ H04N 7/183 348/65 |
| 2012/0314049 | A1* | 12/2012 | Gu ...................... G02B 21/365 348/79 |
| 2013/0201310 | A1* | 8/2013 | Jung ..................... A61B 1/041 348/65 |
| 2015/0016700 | A1* | 1/2015 | Drozdzal ............... G16H 40/63 382/128 |

FOREIGN PATENT DOCUMENTS

| | | | |
|---|---|---|---|
| EP | 1918870 A1 * | 5/2008 | ......... A61B 1/00009 |
| EP | 1918870 | 7/2008 | |
| JP | 57-45833 | 3/1982 | |
| JP | 4-109927 | 4/1992 | |
| JP | 2004/321603 | 11/2004 | |
| JP | 2004/337596 | 11/2004 | |
| JP | 200950856 | 3/2007 | |
| JP | 2010094185 | 4/2010 | |
| WO | WO 00/58967 | 10/2000 | |
| WO | WO 01/65995 | 3/2001 | |
| WO | WO 02/26103 | 9/2001 | |
| WO | WO 02/10223 | 5/2002 | |
| WO | WO2009/008125 | 1/2009 | |
| WO | WO 2011/118288 | 9/2011 | |

OTHER PUBLICATIONS

U.S. Appl. No. 13/729,263, filed Oct. 14, 2014, Peleg.
Vu et al., "Contraction Detection in Small Bowel from an Image Sequence of Wireless Capsule Endoscopy", Proceedings of MIC-CAI'07; vol. 1. (2007), p. 775-783.
Vu et al., "Detection of contractions in adaptive transit time of the small bowel from wireless capsule endoscopy videos", Computers in Biology Medicine 39 (2009), p. 16-26.
Vilarino et al., "Intestinal Motility Assessment With Video Capsule Endoscopy: Automatic Annotation of Phasic Intestinal Contractions" IEEE Transactions on Medical Imaging, vol. 29, No. 2, (Feb. 2010), p. 246-59.
Frohlich et al. "Exploring Geo-Scientific Data in Virtual Environments", ACM Proc. Conf. on Vis., Nov. 1999 p. 169-173, Figs. 4-5.
Economides et al. "Advances in Production Engineering", Web, Sep. 11, 2003, http://pumpjack.tamu.edu/-valko/CV/ValkoPDF/CanadianInvPaper.pdf.
Nuntius et al., "Multimedia Technology, H.264—A New Technology for Video COmpression", p. 1-4.
Lewis, "The Utility of Capsule Endoscopy in Obscure Gastrointestinal Bleeding" Techniques in gastrointestinal Endoscopy, vol. 5, No. 3 Jul. 2003, p. 115-120.
Yoshitaka et al., "Content-Based Retrieval of Video Data by the Grammar of Film" Sep. 1997, 1997 IEEE Symposium on Visual Languages Proceedings, p. 310-317.
Davidson et al., "Multi-viewing of video streams: a new concept for efficient review of capsule endoscopy studies", Gastrointestinal Endoscopy; 2003, vol. 57, No. 5, p. AB 164.

* cited by examiner

SYSTEM AND METHOD FOR DISPLAYING AN IMAGE STREAM

CROSS-REFERENCE TO RELATED APPLICATIONS

This application is a National Phase Application of PCT International Application No. PCT/IL2013/050550, entitled "SYSTEM AND METHOD FOR DISPLAYING AN IMAGE STREAM", International Filing Date Jun. 27, 2013, published on Jan. 3, 2014 as International Publication No. WO 2014/002096, which in turn clams priority from U.S. Patent Application No. 61/666,142, filed Jun. 29, 2012, all of which are incorporated herein by reference in their entirety.

FIELD OF THE INVENTION

The present invention relates to a method and system for image processing of an image stream captured, for example, in-vivo. More specifically, the present invention relates to systems and methods for generating a summarized representation of images and/or events in an image stream of, for example, a gastrointestinal tract and to systems and methods for displaying a dynamic preview representation of a stream of images.

BACKGROUND OF THE INVENTION

The human gastrointestinal (GI) tract refers to the organs found from the mouth to the anus. The small bowel is a part of the GI tract, connecting the stomach with the large intestine. The length of the small intestine in an adult is variable, and measures 7 meters in average. The main function of the small bowel is the digestion and absorption of nutrients and minerals found in the food. In order to do so, the small intestine pushes the food through by the means of a physiological mechanism called intestinal motility.

The colon is a subsequent part of the digestive system in most vertebrates. In the colon, water, sodium and some fat soluble vitamins are absorbed. This process occurs due to contractions of the colon which mix the contents of the large intestine back and forth but do not move them forward. A second type of motility that occurs in the large intestine is the high amplitude propagating contraction, which are extremely strong contractions that move the contents of the large intestine forward.

Intestinal motility can be divided into two categories: peristalsis, e.g. synchronized movement of the intestinal wall responsible for moving the food in one direction; and independent contractions, e.g. unsynchronized movement of the intestinal wall where the muscles squeeze substantially independently of each other, which may have the effect of mixing the contents but not moving them forward or backward.

In-vivo imaging methods, such as performed by an in-vivo imaging system including a swallowable capsule, may be used to image body lumens within a patient. The imaging system may capture and transmit, for example, images of the GI tract to an external recording device, while the capsule passes through the GI lumen. The capsule may capture images in variable frame rates of, for example, 1-40 frames per second. Large numbers of images, for example 100,000 to 300,000 images, may be collected for viewing during the imaging procedure, which may be performed in a duration of one to eight hours, and may be viewed and/or processed in real time. The images may be combined in sequence, and an image stream or movie may be presented to a user.

U.S. Pat. No. 7,215,338 to Horn et al., incorporated by reference herein in its entirety, discloses a system and a method for creating a fixed summarized graphical presentation of a data stream captured in-vivo. The graphical presentation may be in the form of a color bar, which may be calculated based on average image pixel values of one or more image frames. However, differentiation between adjacent images may not be detectable in the fixed summarized presentation disclosed by Horn et al., and different characteristics, portions or segments (e.g. lumen hole, tissue, intestinal content) of a single image may not be discernible when a user examines the fixed summarized presentation. Furthermore, the disclosed fixed summarized graphical presentation is not detailed, and does not provide information of contractile activity or motility events. It may therefore be useful to provide a method and system for displaying summarized information of image characteristics in a discernible manner.

Various image properties, intestinal events, contractile activity or motility may be determined using in-vivo image sequences, as disclosed for example in U.S. Pat. Nos. 6,944,316 and/or 7,200,253 to Glukhovsky et al., and in U.S. Pat. No. 7,724,928 to Glukhovsky et al., each of which is being incorporated by reference herein in its entirety. Presentation of motility data in a graphical plot form is disclosed, e.g. in FIG. 3 of U.S. Pat. No. 6,944,316. Due to the large number of images in the stream, such presentation (for the complete image stream) may be difficult to display in a single bar or graph on the monitor. The area required on the screen to present all the available motility data may be too large or too long to fit into a screen display, which may also include, for example, one or more image stream windows and additional medical information provided to the user. It may therefore be required to provide a new display method, which uses an available amount of screen space and is combined with the Graphical User Interface display.

SUMMARY OF THE INVENTION

A computer-implemented method is provided, according to embodiments of the present invention, for displaying a summarized image presentation of sequential images, for example intestinal images captured by an in vivo imaging device. The method may include receiving an image stream captured by, for example, an in vivo device, a video camera, or a security or surveillance camera. The image stream may include digital image frames, each frame may contain a plurality of image pixels arranged in a pixel array. For at least a subset of the image frames, a summarized image presentation comprising summarized data elements such as pixel strips may be generated. Each summarized data element may correspond to or be associated with at least one frame from the image stream. In some embodiments, generating a summarized data element may include ordering pixels of one or more image frames according to a first sorting parameter and sampling the ordered pixels according to a predetermined sampling scheme to acquire a subset of ordered pixels. Each subset of ordered pixels may be combined in a graphical format, e.g. aligned, positioned or arranged adjacently in a pixel strip, line or another spatial arrangement, to form a summarized data element. While in one embodiment a summarized data element is a line, or a series or strip of sub-elements such as pixels, summarized data elements in other forms or shapes may be used. In some embodiments, the summarized image presentation may be presented in the form of a graph, plot, or diagram.

In some embodiments, the summarized presentation may be displayed on a visual display unit (e.g., near or along a video display of the image stream). However, the video display and the summarized presentation need not be contiguous or adjacent to be "along", and in some embodiments are not along or near each other. The video display may include at least one frame being displayed in each time slot, and the frames may be displayed sequentially for example according to their frame capture time or order of capture. The video display may include playing the captured images as a movie, e.g. according to their order of capture, in a fixed or varying frame display rate.

A sorting parameter may be based on a pixel values in one embodiment. For example, chroma-related (e.g. color purity) pixel values, such as red/green value of pixels represented in a red-green-blue (RGB) color space, or H value of pixels represented in a hue-saturation-value (HSV) color space. Some embodiments may include ordering (or re-ordering) pixels of one or more image frames according to a second sorting parameter, which may be based on pixel values, e.g. luminance or intensity-related pixel values. Examples of a second sorting parameter include R in an RGB color space, or V in HSV color space. Other color spaces and/or other sorting parameters may be used.

In another example, sorting parameters may be based on scores of one or more feature detectors which may be applied to image frames. In one example, a turbid content detector may produce content scores per pixel, and the scores may be used as a sorting parameter. In some embodiments, a lumen hole may be detected in image frames and the lumen detection scores per pixel may be used as a sorting parameter. Other detectors and/or other scores may be used. In some embodiments sorting parameters may be based on a combination of detector scores and pixel values. More than one or two sorting parameters may be used. In some embodiments, certain image characteristics, properties and/ or intestinal events may be determined, e.g. automatically by a processing unit, based on a summarized image representation or portions thereof.

A system and method for dynamically displaying detailed preview of at least a portion of an image stream is also presented. A dynamic preview presentation, e.g. a dynamic preview bar, may be calculated and displayed to a user in a continuously or intermittently changing manner. The image stream may be displayed as a video stream or movie, for example simultaneously or alongside and in correlation with the summarized image preview presentation. A dynamic preview of a current portion of an image stream may be generated, and may be updated or adjusted as the image stream continues, or when a user indicates a portion of the stream to be previewed (e.g. by pointing with an input device or hovering over a summarized graphical presentation, for example). The dynamic preview presentation may be correlated to one or more image frames which may be substantially concurrently or simultaneously displayed in a video display of the image stream. The dynamic preview presentation may include a detailed data segment, which is associated with at least one frame simultaneously being displayed in the video display window or portion of the display screen, and frames adjacent to the at least one frame being displayed. The dynamic preview presentation may also include a reduced data segment. In some embodiments, the dynamic preview presentation may be displayed, e.g. on a visual display unit, along the video display of the image stream.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1A:
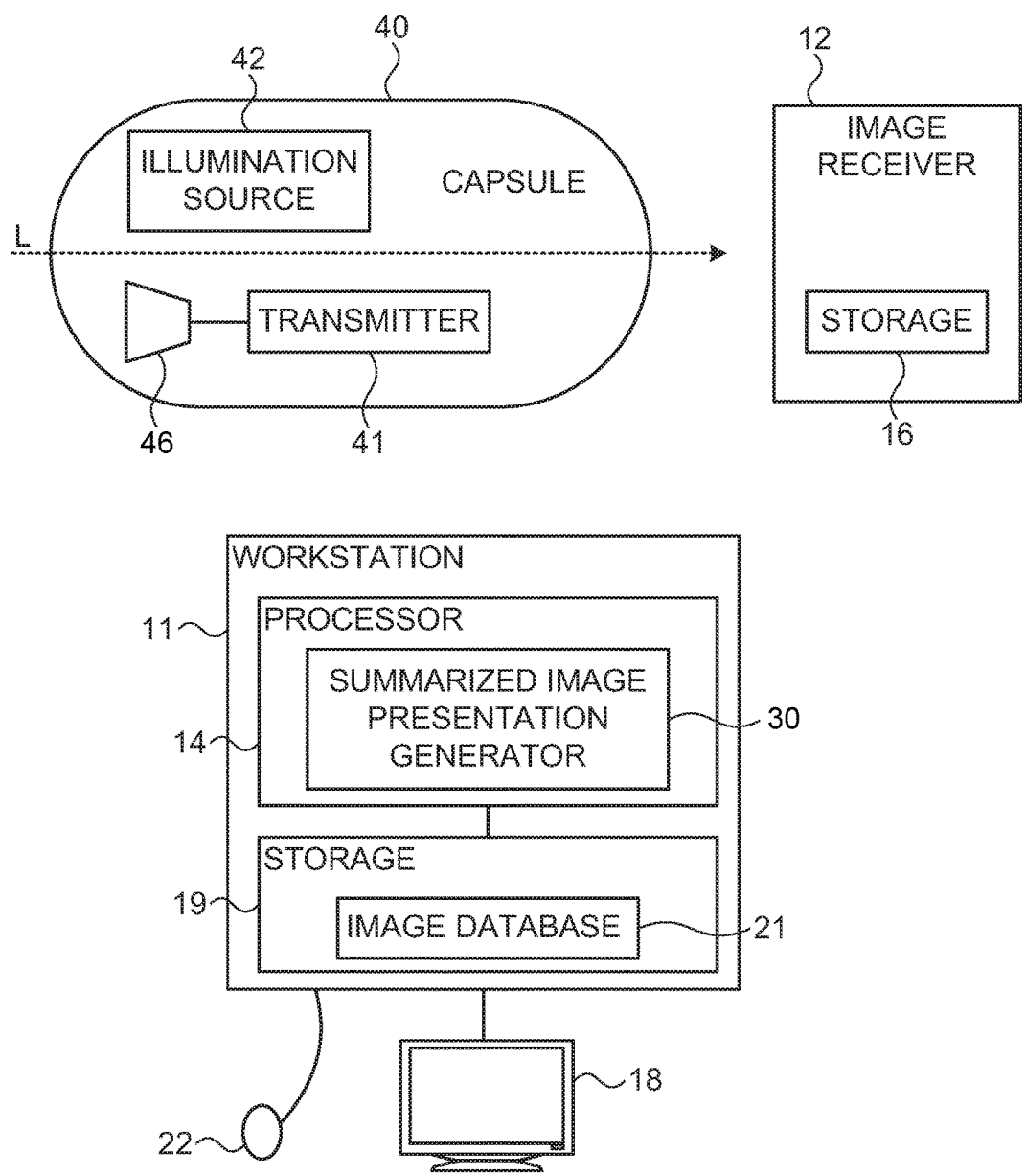
FIG. 1A shows a schematic diagram of an in-vivo imaging system for generating a summarized image presentation according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. Embodiments of the invention may include an article such as a computer or processor readable non-transitory storage medium, such as for example a memory, a disk drive, or a USB flash memory encoding, including or storing instructions, e.g., computerexecutable instructions, which when executed by a processor or controller, cause the processor or controller to carry out methods disclosed herein.

Devices according to embodiments of the present invention, including imaging, receiving, processing, storage and/or display units suitable for use with embodiments of the present invention, may be similar to embodiments described in U.S. Pat. No. 7,986,337 to Davidson et al. entitled "System and Method for Editing an Image Stream Captured In-Vivo", U.S. Pat. No. 7,009,634 to Iddan et al., entitled "Device for In-Vivo Imaging", and/or US Patent Application Publication Number 2007/0118012 entitled "Method of Assembling an In-Vivo Imaging Device", each assigned to the common assignee of the present application and incorporated by reference herein in its entirety.

Of course, devices and systems as described herein may have other configurations and other sets of components. Devices, systems and methods according to some embodiments of the present invention may be similar to the commercial PillCam® SB2 or PillCam® Colon capsules and the associated data recorders and RAPID® workstations provided by Given Imaging, Ltd.

An in vivo imaging capsule which may be swallowed by a patient, may be maneuvered or may progress passively along the GI tract, due to peristaltic contractions which move the intestinal tissue walls. During its journey, the capsule passes through different GI organs, such as the esophagus, the stomach, the small bowel and the colon. Due to the relatively narrow tunnel structure of the small bowel tissue walls, while the capsule is traveling in the small bowel, it may maintain a position which is parallel to the direction of the tunnel. The longitudinal axis of the imaging capsule (e.g., an axis passing through the long dimension of the capsule, such as axis L in FIG. 1A) may generally remain parallel to the direction that the capsule advances in the small bowel. The imaging system of the capsule may be positioned in at least one of the longitudinal ends of the capsule, such that the imaging is performed generally in a forward and/or backward looking direction of the small bowel tunnel, such that images of the opening and closing of the lumen walls are captured quite regularly. Image data capturing the opening and closing of the lumen walls, in combination with the recordation of the time of capturing each image, may permit analysis, display and/or calculation of the small bowel's motility events, or type and frequency of peristaltic activity. Embodiments of the invention may enable display of motility-related information to a medical professional in an efficient and easy to analyze way.

Detection and characterization of specific events of intestinal motility is known in the area of intestinal motility, such as intestinal contractions detection in "Contraction detection in small bowel from an image sequence of wireless capsule endoscopy" to Vu, H., Echigo, T., et al. (in Proceedings of MICCAI'07; vol. 1. 2007, p. 775-783), "Detection of contractions in adaptive transit time of the small bowel from wireless capsule endoscopy videos" to Vu, H., Echigo, T., Sagawa, R., Yagi, K., Shiba, M., Higuchi, K., et al. (Comput Biol Med 2009; 39:16-26), and "Intestinal motility assessment with video capsule endoscopy: automatic annotation of phasic intestinal contractions" to Vilarino, F., Spyridonos, P., Deiorio, F., Vitria, J., Azpiroz, F., Radeva, P. (IEEE Trans Med Imaging 2010; 29(2):246-59).

When a professional reviewer, e.g. physician, reviews a GI imaging procedure, it may be useful to provide detailed informative data regarding the imminent or upcoming frames which will be viewed. A large number of images, e.g. 100,000 images, may be captured during an imaging procedure. Summarizing data from all these images in a fixed motility display along the image stream window on a monitor having conventional dimensions and resolution may not provide detailed information regarding frame characteristics of a smaller, relevant subset of the image stream, e.g., 20 frames surrounding the presently viewed image, since, in view of screen size and resolution parameters, each strip of pixels comprising the fixed motility display may summarize data of a larger subset of frames, e.g. 100 frames. Some events which may be significant for diagnosis, such as motility events of the patient's GI tract or small regions in the GI tract with much intestinal content, may not be clearly visible in a fixed display, since the resolution of a fixed display is limited. Such events may be captured over a relatively small number of images, e.g. less than 20 images. The change of scenery during those frame sequences may be quite substantial, for example a contraction may be captured over a sequence of, e.g., 10 frames, and the lumen hole which appears in the images may be large in the first image of the frame sequence, growing smaller towards the middle of the sequence, and growing larger towards the end of the sequence. Therefore, displaying a detailed preview of data corresponding to a small number of images (e.g. the upcoming next few frames) during review of an image stream may provide enhanced visual display of intestinal regions of interest or points of interest throughout the imaging procedure.

Embodiments of the present invention describe a system and method for displaying a summarized presentation of image data, based on analysis and processing of data extracted from image frames captured in the GI tract. Each image frame may be represented as a two-dimensional array of pixels, for example a rectangular or square pixel array of a certain height and a certain width (e.g., 320×320 pixels). Each pixel may consist of one or more bits of information, representing the brightness of the image at that point and possibly including color information which may be encoded as RGB triplets.

Analysis and processing of the image data may be performed automatically by a processing device, without user intervention. The summarized display of image data, for example using a summarized bar, window or display including for example summarized pixel strips or other arrangements of summarized image data, may be performed, e.g., by one or more processors, a workstation, circuitry, a detector or any other computation device. According to some embodiments of the present invention, one or more summarized display windows or bars may be displayed to a health professional for diagnosis, using a dynamic or a fixed display.

Data of images may be summarized, and an indication of image pixels corresponding to various structures or contents depicted in the image may be presented to a user. According to embodiments of the invention, images of intestinal tissue may be segmented into different categories. The categories may include different types of visible structures depicted in the image frame or specific pixel characterisitics. The following categories are examples of segment types which may be detected in an intestinal image:

1) lumen hole—portion of the image which may be substantially darker than the rest of the image and depicts the opening of the tissue walls;

2) "tissue walls"—image portions which depict tissue walls; and

3) "turbid content"—lumen hole and/or tissue wall occluded by intestinal content.

Other categories may be used in addition or instead.

Obtaining a significant amount of image data may allow a detailed analysis of physiological structures or events. However, large amounts of the data may require a long duration of video visualization, and the diagnosis of a patient's imaging procedure by the physician may take a relatively long time. It may be useful to provide a dynamic preview bar or display, which shows informative data representing upcoming images in the image stream reviewed by a medical professional.

Intestinal events may be related to sequences of images which may have a certain pattern or a specific motility-related property which may be depicted in a sequence of consecutive images from the image stream. For example, an intestinal event may include intestinal contractions, which may be detected as a sequence of images depicting a pattern of an open-closed-open lumen hole. In another example, an intestinal event may include periods of static lumen walls (e.g. repeated images of an open lumen hole which may be referred to as an open tunnel sequence) or a closed lumen hole. Another type of intestinal event is a turbid or occluded lumen opening, indicating presence of intestinal content in the images. Other types or categories of events may be detected based on images of the image stream.

Reference is made to FIG. 1A, which shows a schematic diagram of an in-vivo imaging system for generating a summarized image presentation according to an embodiment of the present invention. In an exemplary embodiment, the system includes a capsule 40 having one or more imagers 46, for capturing images, one or more illumination sources 42, for illuminating the body lumen, and a transmitter 41, for transmitting image and possibly other information to a receiving device. Typically, the image capture device may correspond to embodiments described in U.S. Pat. No. 7,009,634 to Iddan et al., and/or in U.S. Patent Application Publication No. 2007-0118012 to Gilad, each of which incorporated by reference herein in its entirety, but in alternate embodiments may include other sorts of image capture devices. The images captured by the imager system may be of any suitable shape including for example circular, square, rectangular, octagonal, hexagonal, etc. Typically, located outside the patient's body in one or more locations are an image receiver 12, typically including an antenna or antenna array, an image receiver storage unit 16, a data processor 14, a data processor storage unit 19, and an image monitor or visual display unit 18, for displaying, inter alia, images recorded by the capsule 40. Typically, data processor storage unit 19 includes an image database 21.

Typically, data processor 14, data processor storage unit 19 and monitor 18 are part of a personal computer or workstation 11, which includes standard components such as processor 14, a memory, a disk drive, and input-output devices (e.g., 22) such as a mouse and keyboard, although alternate configurations are possible. Data processor 14 may include any standard data processor, such as a microprocessor, multiprocessor, accelerator board, or any other serial or parallel high performance data processor. Data processor 14, as part of its functionality, may act as a controller controlling the display of the images (e.g., which images, the location of the images among various windows, the timing or duration of display of images, etc.). Image monitor 18 is typically a conventional video display, but may, in addition, be any other device capable of providing image or other data. The image monitor 18 presents image data, typically in the form of still and moving pictures, motility data and in addition may present other information. In an exemplary embodiment, the various categories of information are displayed in windows. A window may be for example a section or area (possibly delineated or bordered) on a display or monitor; other windows may be used. Multiple monitors may be used to display image frames, summarized image presentations, motility properties, motility events and other data. In one embodiment an image monitor may also be included in image receiver 12.

During an image capturing procedure, imager 46 captures images and may send data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 may be sent to the data processor 14 or the data processor storage unit 19. For example, the image receiver 12 or image receiver storage unit 16 may be taken off the patient's body and connected to the personal computer or workstation which includes the data processor 14 and data processor storage unit 19 via a standard data link, e g, a serial, parallel, USB, or wireless interface of known construction. The image data is then transferred from the image receiver storage unit 16 to an image database 21 within data processor storage unit 19. Typically, the image stream is stored as a series of images in the image database 21, which may be implemented in a variety of known manners. Data processor 14 may analyze the data and provide the analyzed data to the image monitor 18, where a user views the image data. For example, data processor 14, or another data processor (e.g. in receiver 12) may process images and create an intestinal events bar according to embodiments of the present invention. Data processor 14 operates software that, in conjunction with basic operating software such as an operating system and device drivers, controls the operation of data processor 14. Typically, the software controlling data processor 14 includes code written in the C++ language, and may be implemented using various development platforms such as Microsoft's .NET platform, but may be implemented in a variety of known methods.

The image data recorded and transmitted by the capsule 40 may be digital color image data, and may be captured for example in an RGB (Red, Green, Blue) color space, although in alternate embodiments other image formats may be used. In an exemplary embodiment, each frame of image data includes 320 rows of 320 pixels each (e.g., 320 rows and 320 columns), each pixel including bytes for color and brightness, according to known methods. For example, each imager pixel may include a color sensor which may correspond to a single primary color, such as red, green, or blue. The brightness of the overall pixel may be recorded by a one byte (i.e., 0-255) brightness value. Images may be stored, for example sequentially, in data processor storage unit 19. The stored data is comprised of one or more pixel properties, including color and brightness. Other formats for image representation may be used. Alternatively, in each pixel, data may be represented by cylindrical-coordinate representation formats such as hue, saturation and lightness (HSL or HLS), hue, saturation and value or brightness (HSV or HSB), or hue, saturation and intensity (HIS). Cylindrical-coordinate representations of the RGB color space are characterized by representing the color or hue information by the angle around a central vertical axis while the distance from the axis corresponds and the distance along the axis corresponds to other information such as saturation and brightness. For example, when using HSV representation, a hue (H) value may represent the angle around the central vertical axis a saturation (S) value may represent the distance from the axis, and a value (V) may represent the distance along the axis. Alternatively, other representations may be used, such as YCbCr (Y is the luminosity or luminance component and Cb and Cr are the blue-difference and red-difference chroma components), Lab color space etc. According to one embodiment, images may be stored for example sequentially in data processor storage unit 19. The stored data may include one or more pixel properties, including H, S and V.

Data processor storage unit 19 may store a series of images recorded by a capsule 40. The images the capsule 40 captured, for example, as it moves or is maneuvered through a patient's GI tract, may be combined consecutively to form a series of images displayable as an image stream. When viewing the image stream, the user is typically presented with one or more windows on monitor 18; in alternate embodiments multiple windows need not be used and only the image stream may be displayed. In an embodiment where multiple windows are provided, for example, an image window may provide the image stream, or still portions of that image. Another window may include buttons or other controls that may alter the display of the image; for example, stop, play, pause, capture image, step, fast-forward, rewind, or other controls. Such controls may be activated by, for example, a pointing device such as a mouse or trackball. Typically, the image stream may be frozen or paused to view one frame, speeded up, or reversed; sections may be skipped; or any other method for viewing an image may be applied to the image stream.

Image properties and/or intestinal (e.g. motility) events may be detected based on one or more consecutive images from the image stream. According to embodiments of the invention, visual detection of image properties and/or of defined sequences in an image stream may be correlated to or associated with certain properties or sequences in a summarized presentation. The summarized presentation may be used for visualization of image properties such as the amount of intestinal content in the images, motility events which occurred during the imaging procedure, and/or determination of motility properties of the imaged lumen (e.g. may indicate abnormal motility). Visual detection of one or more of the following image properties and/or intestinal event sequences may be performed (by the reviewer, or automatically by a processor): turbid frames (with a substantial percentage of intestinal content), relaxed lumen sequences, or contractions. Other image properties and/or sequence categories may be used. In this context the detection may include, for example, indicating which frames are occluded by intestinal content, and marking the beginning and the end of each type of sequence, or correlating a start image and an end image from the image stream to each type of sequence. In another example, images in the image stream may be categorized or attributed as belonging to one or more categories (e.g. associated with certain image properties and/or types of event sequences).

A summarized presentation or display may include multiple summarized image elements. While a summarized presentation may be formed in one embodiment as a "bar", displays or organizations of visual data other than a bar, and in shapes other than a bar, may be used as a summarized display. Data processor 14 may include, or may be operationally connected to, a summarized image presentation generator 30. Summarized image presentation generator 30 may process images from the captured set of images, and may obtain visual properties or portions of the images for display in a preview portion of the Graphic User Interface (GUI). Summarized image presentation generator 30 may produce a plurality of summarized data elements (e.g., strips), each element summarizing data of one or more captured images. The summarized data may be computed based on, for example, pixel characteristics of images from the image stream. The summarized data elements may be combined, e.g. aligned or positioned adjacently and combined, appended, or merged to form a summary bar. Data processor 14 and/or display 18 may include or may be configured to execute graphics software or hardware for generating the summarized presentation.

In order to generate a summarized presentation, a set of images from the image stream may be provided to summarized image presentation generator 30. The set of images may include, for example, all images captured by the imaging device. In some embodiments, a subset of images may be used for generation of a summary bar. The subset of images may be selected, for example according to predetermined selection criteria.

In some embodiments, the summarized presentation or display may be generated for selected portions of the GI tract. For example, the summarized presentation may be generated for selected organs (esophagus, small bowel, colon, stomach, etc.), or for a selected duration of time from the complete imaging procedure (for example, the first 2 hours). According to embodiments of the invention, motility events or motility properties may be detected based on images from an image stream, e.g. selecting image frames or image sequences (e.g. a series of sequential image frames from an image stream, which may include for example a number of consecutive frames selected from the image stream).

In one example, a subset of images used for generating a summarized presentation may include images captured between certain points of interest which may be identified in the image stream. In some embodiments, anatomical landmarks or pathologies may be selected as points of interest, e.g. anatomical landmarks such as the duodenum, the cecal valve, the Z-line (indicating entrance to the stomach), etc. Two points of interest in the captured image stream may be selected (e.g. may be predetermined in the system, or selected by a user reviewing the image stream) and all images captured during the time the capsule traveled between a first selected point to a second selected point may be included in the generation of a summarized presentation. In some embodiments, the summarized presentation may be generated for images of the small bowel, e.g. for the portion of the imaging procedure which was captured between the first duodenal image and the first cecal image.

Images for generation of a summarized presentation may be selected from the complete set of captured images according to predetermined criteria. In some embodiments, certain images may be excluded from the image stream, e.g. images which are too dark or too bright. Methods similar to those described in U.S. Pat. No. 7,986,337 to Davidson et al., which discloses embodiments of editing methods of an in vivo image stream to create a reduced movie may be used to select images for generation of a summarized presentation. The images selected for a reduced image stream may be used for generating the summarized presentation. In yet another example, images may be merged or fused, e.g. based on similarity between adjacent images, and a summarized presentation, e.g. in the form of a summary bar, may be generated based on the subset of fused or merged images. Other image selection methods may be used for determining the subset of images. In some embodiments, different image selection methods may be combined, for producing the subset of images which may be used in the generation of a summarized presentation.

Figure 2A:
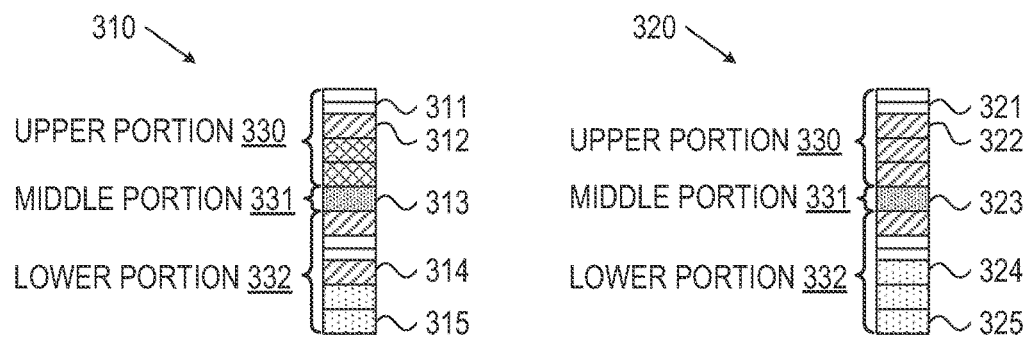
FIG. 2A shows two exemplary elements of summarized image data according to an embodiment of the present invention.

The summarized image presentation generator 30 may generate summarized data representing an image or a group of images of the selected set of images (e.g. each image in a complete image stream or in a reduced image stream). The summarized data may be generated, for example, in the form of a strip of pixels. When used herein, a "strip" of pixels may include a stripe element of a displayed summarized presentation. The strip may include a plurality of adjacent pixels arranged in a line, with pixel values which may be computed using pixel parameters from the one or more image frames which are summarized in the strip. The strip may be generated in various methods. A strip is typically rectangular, and may be of a certain pixel length and a width of one or more pixels. Exemplary strips are shown in FIG. 2A. Elements making up summarized presentations or displays other than strips or stripes may be used, having shapes other than a strip or stripe. Each pixel element or strip may correspond to, show data derived from, or be associated with one or more frames.

In some embodiments, a subset of pixels of an image or of a plurality of images may be selected for generation of a summarized data element. For example, a fixed template or mask may be defined for an image stream, to specify or select a region of interest which is selected from each image. The region of interest may be defined based on known optical properties and/or illumination properties of the imaging system of capsule 40. Generation of the summarized data element, e.g. pixel strip, may be performed based on the subset of pixels included in the region of interest. In one example, a captured image may be shaped as a circle of for example 320 pixels in diameter, and a region of interest in the image may be defined as a smaller circle (e.g. of 200 pixels in diameter), which is centered in the captured image. The region of interest in the image may be selected such that mostly central pixels are selected from the image, and darker pixels (which are in the peripheral region of the image) are not selected. Such pixel selection may assist in avoiding misrepresentation of a lumen hole in the image, which may be caused due to insufficient illumination of the in vivo scene rather than an actual lumen hole depicted in the image.

Lumen hole detection in images may be used to generate summarized preview data of one or more image(s). In order to provide preview information of an image or a plurality of images in a summarized form, it may be useful to distinguish between pixels that are likely to depict a lumen hole and pixels that are likely to depict tissue or intestinal content. The distinction (e.g. classification) between these pixel types may be performed, for example, by summarized image presentation generator 30, and may be used to generate a summarized data strip indicating a lumen hole and its relative size and/or position in the represented image(s). In one embodiment, RGB values of image pixels may be used to detect a lumen hole in one or more images. In another embodiment, lumen detection may be based on edge detection methods or wrinkle detection (e.g. as disclosed in US Patent Application Publication Number 20110044515 to Spyridonos et al., assigned to the common assignee of the present application). The size or size estimation of a detected lumen hole in a sequence of images may indicate a contraction, a tunnel sequence, or other motility-related intestinal events. Different parameters may be combined to detect the lumen hole in the images, e.g. detection may be based both on RGB pixel properties and on edge detection.

Motility information may be based on the size of the lumen hole which is visible in the images. For example, a contraction may be detectable in a sequence of images which may depict a large lumen hole in the first images, which gradually becomes smaller towards the peak of the contraction (in subsequent images), and grows larger again when the contraction ceases. An exemplary contraction sequence is shown in FIG. 2 of US Patent Application Publication Number 20090284589 to Radeva et al., assigned to the common assignee of the present application.

In one embodiment, summarized image presentation generator 30 may sort selected pixels of an image frame (or plurality of frames) according to at least one pixel parameter value. Different pixel parameter values may be used, for example R, G or B values of the pixels (represented in an RGB color space) or any linear or non-linear combination thereof, or luminance or chrominance values which may be computed based on pixels converted to a different color space (e.g., a chrominance-luminance color space such as HSV, HSB, etc.). The sorted pixels may be sampled according to a predetermined sampling scheme. The sampled pixel values may be used for generating a summarized presentation element, e.g. in the form of a pixel strip which will be displayed in a summarized presentation of the image stream.

Other methods may be used to generate summarized data elements of a summarized presentation or display. In some embodiments, a lumen hole may be detected in each image, and its area may be determined. The determined area may be a relative size, for example the ratio or percentage of the number of pixels that the lumen hole occupies within an image, or may be an estimation of an absolute (e.g. actual) area of the lumen hole depicted in the image. In one embodiment, if only a portion of the lumen hole is depicted, an estimation of the portion of image that the lumen hole would occupy if the hole was portrayed completely in the image may be provided, and the estimated lumen area value may be used for generating a summarized data element for an image.

Figure 1B:
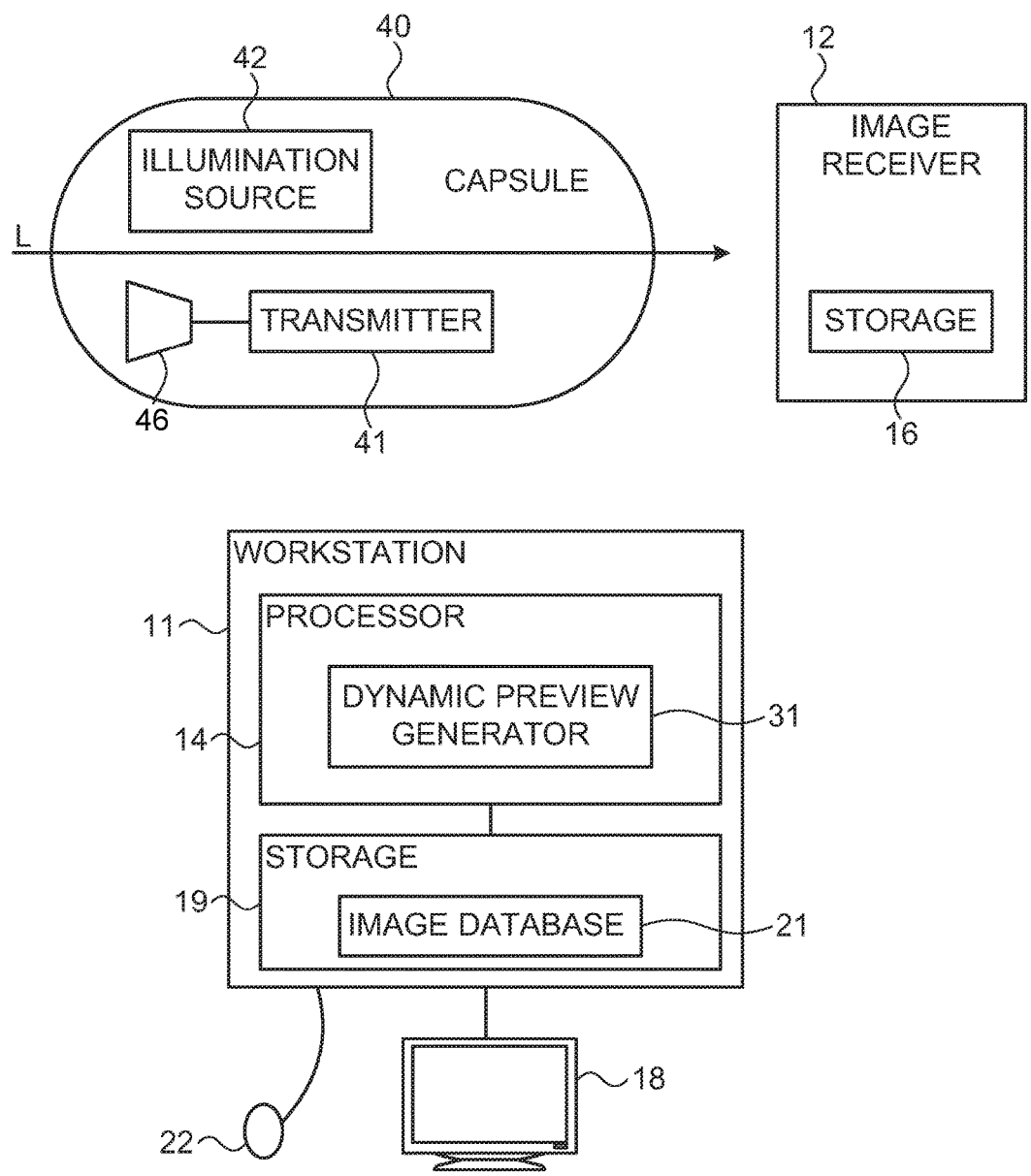
FIG. 1B shows a schematic diagram of an in-vivo imaging system for generating a dynamic preview presentation according to an embodiment of the present invention.

The generation of a summarized presentation of images, e.g. in vivo images, may be fixed or dynamic. Reference is now made to FIG. 1B, which schematically illustrates an in-vivo imaging system for generating a dynamic preview presentation according to an embodiment of the present invention. Elements of FIG. 1B are similar to those of FIG. 1A, and reference numerals are repeated among the figures to indicate corresponding or analogous elements.

A dynamic preview bar may allow a user to examine a detailed preview of information corresponding to one or more image frames. Information such as pixel data, pixel properties, structures depicted in the images, image characteristics or other features detected in an image may be indicated in the detailed preview. The method and system described herein for dynamic display of a summarized presentation of an image stream may be applied to various summarized presentations or bars, such as, for example, the summarized presentation disclosed herein, a graphical summarized presentation as disclosed in U.S. Pat. No. 7,215,338, a graphical summarized presentation as disclosed in US Patent Application Publication Number 2007/0060798, or other summarized data bars which may contain summarized data corresponding to a large amount of in vivo images.

A dynamic preview generator 31 may be used to create and/or display a preview bar dynamically. The process of generating and/or displaying a summarized presentation of an image stream may be a dynamic, on-going task which is (substantially) continuously or repeatedly performed by dynamic preview generator 31, for example during display of the image stream to a user, and a dynamic preview bar may be continuously or repeatedly updated. Continuous updating in this sense may mean repeatedly, e.g., every N seconds or every N microseconds, or some other fixed or variable interval. For each frame (or group of frames) which may currently be displayed in an image stream viewing window, a dynamic preview bar may be adjusted, updated or recalculated and displayed to the user, in order to provide a detailed, close-up or zoomed-in preview of adjacent or upcoming frames of the image stream. A less detailed preview, of image frames which were captured during earlier or later periods of the imaging procedure, may be provided in the same preview bar.

The recalculated dynamic preview bar may provide, per each frame or group of frames, informative data to the procedure reviewer, such as a preview or indication of various structures which may be depicted in the images, indication of the amount of intestinal content, contractions, or other motility events which may be detectable by examination of a detailed segment of the preview bar which is correlated to or associated with a portion of the image stream, e.g. the currently displayed frame(s) of the image stream and adjacent frames. The dynamic preview bar may be updated or recalculated frequently or continuously, e.g. for every displayed image frame, so the user may see a preview of the upcoming frames (e.g., upcoming 100 frames) in a detailed format which enables detecting intestinal events which may occur over a relatively small amount of frames (e.g., over 10 frames). In other embodiments, the dynamic preview bar may be updated or recalculated for groups of a predetermined number of frames, e.g. once every 5 displayed frames, or at constant time intervals e.g. once every 30 seconds.

A dynamic summarized presentation, e.g. a dynamic preview bar, may be divided into two or more segments. A first segment may include a detailed data segment, corresponding to one portion of the image stream, and a second segment may include a reduced data segment, corresponding to other portions of the image stream. The dynamic preview bar may provide extended preview information in the detailed data segment, for example relating to a relevant portion of the image stream, or associated with images from the image stream being concurrently, simultaneously or substantially simultaneously displayed in an image stream window. In some embodiments, the detailed data segment may be calculated and displayed according to a user's selection of a portion of the image stream, e.g. selecting an image frame or a segment from the image stream using an input device such as a mouse, joystick, touchscreen, etc. Reduced preview data which is associated with other portions of the image steam (e.g. portions which are not being concurrently displayed, or portions which were captured a certain amount of time before or after image frames being concurrently displayed) may be displayed as well, for example along the detailed segment or situated in the vicinity of the detailed segment, in a single dynamic summarized presentation.

More than two segments may be provided in a dynamic preview bar, and the level of detail displayed in the dynamic preview bar for each portion of the image stream may change in each segment. For example, a first segment may have a first level of detailed data, a second segment may include a second level of detailed data, and so forth. Each level of data may be less detailed or reduced in the amount of detail provided to the user, in comparison to the previous level of detail. As such, the first level of detail may provide the most detailed data corresponding to a first portion of the image stream, the second level may provide less detailed data corresponding to a second portion of the image stream, and the last level of detail may provide the least amount of detail corresponding to the portion of the image stream associated with it. In one embodiment, the first level of detail is associated with a portion of the image stream which may be concurrently or simultaneously displayed in an image stream window, and the other levels of data may correspond to portions of the image stream which were captured later or earlier in the imaging procedure.

Figure 6A:
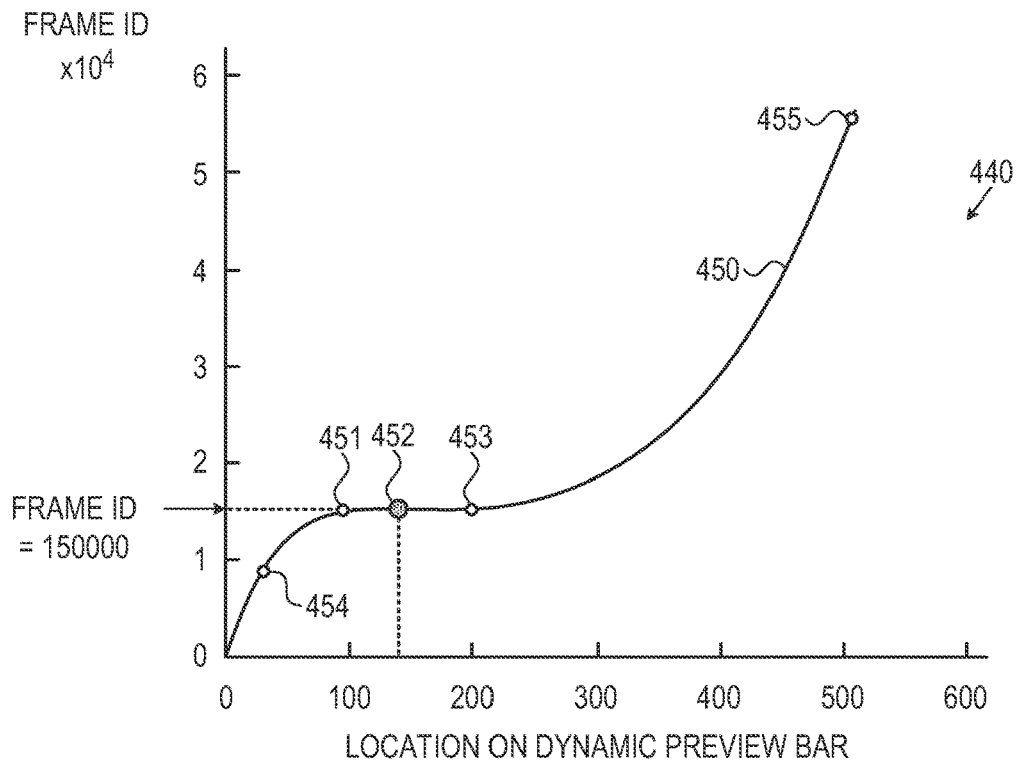
FIGS. 6A and 6B present exemplary graphs of time distortion of image stream frames represented in a dynamic preview presentation, according to an embodiment of the present invention.
Figure 6B:
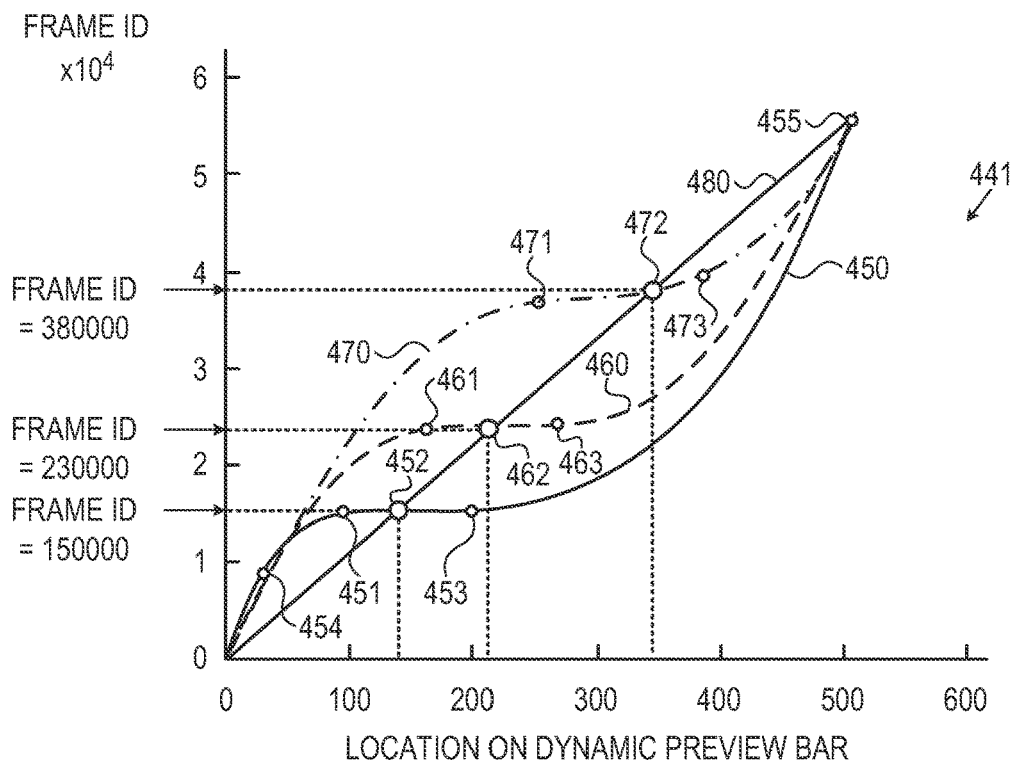

In some embodiments, the level of detail of data in the preview bar may be gradually increasing or decreasing according to the time of capture of the image frames. E.g., frames captured adjacently to a currently displayed frame in an image stream window may be displayed with high level of detail, and frames captured a short time later or earlier may be displayed with a gradually decreasing level of detail in the dynamic preview bar. As the distance (e.g. measured in time) of the frame from a current frame displayed in or selected by a user increases, the corresponding level of detail displayed in the associated segment of the dynamic preview bar may decrease. In some embodiments, the frame identification number or frame capture time may be assigned to a specific level of detail in the corresponding segment of the dynamic preview bar, e.g. according to a predetermined function, as illustrated in FIGS. 6A and 6B herein.

Dynamic preview generator 31 may compute an initial preview bar for the image stream. The initial preview bar may be comprised of preview bar elements, e.g. summarized data elements 310 and 320, and each element may be calculated for one or more image frames. Other methods may be used to calculate preview bar elements of the initial preview bar. Dynamic preview generator 31 may generate an initial preview bar with no time distortion between represented image frames, e.g. each preview bar element may represent the same amount of frames from the image stream. The initial preview bar may be fixed or static.

Figure 5A:
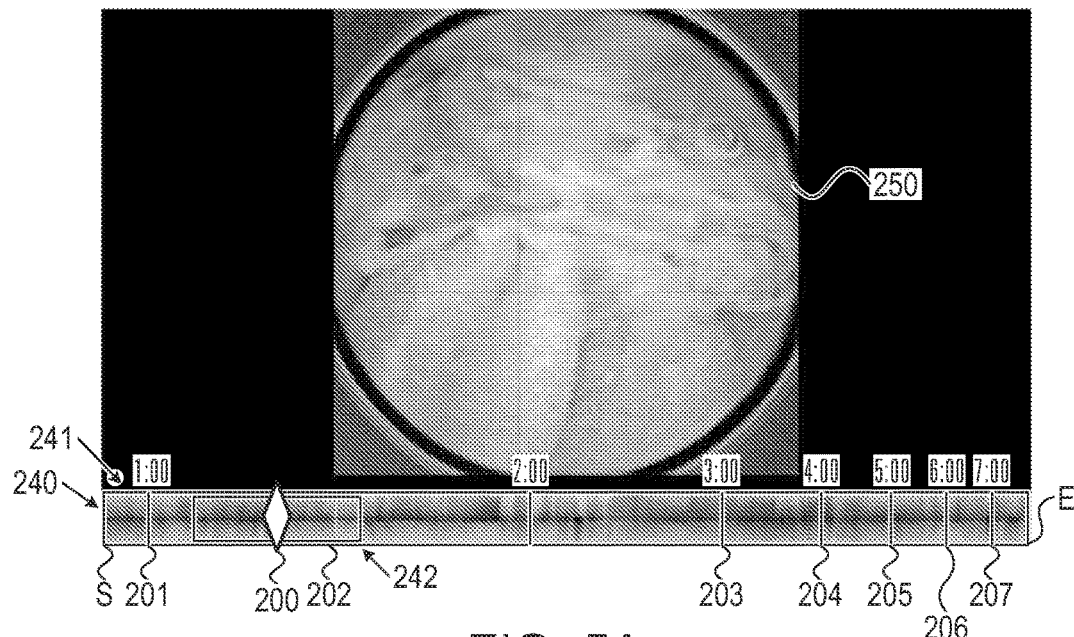
FIGS. 5A-5D show different dynamic preview bars of an image stream according to an embodiment of the present invention.
Figure 5B:
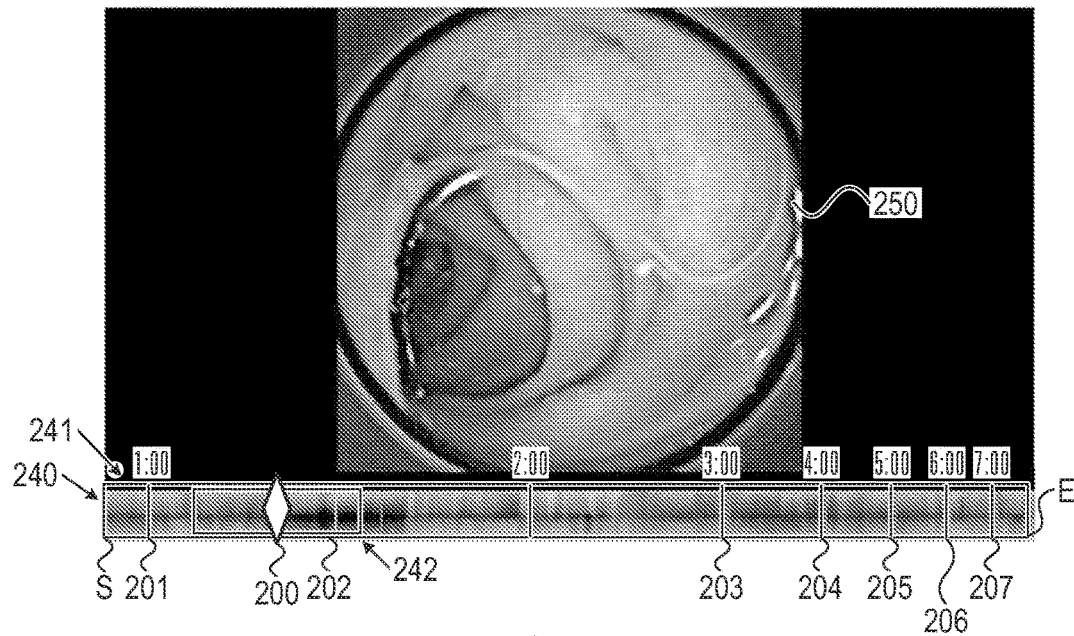
Figure 5C:
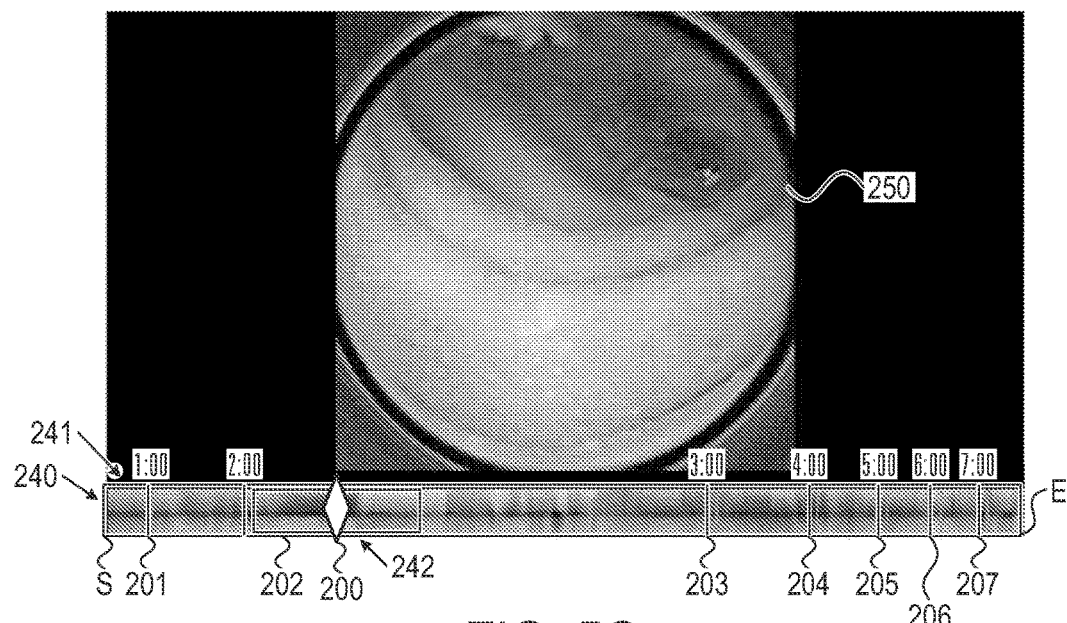
Figure 5D:
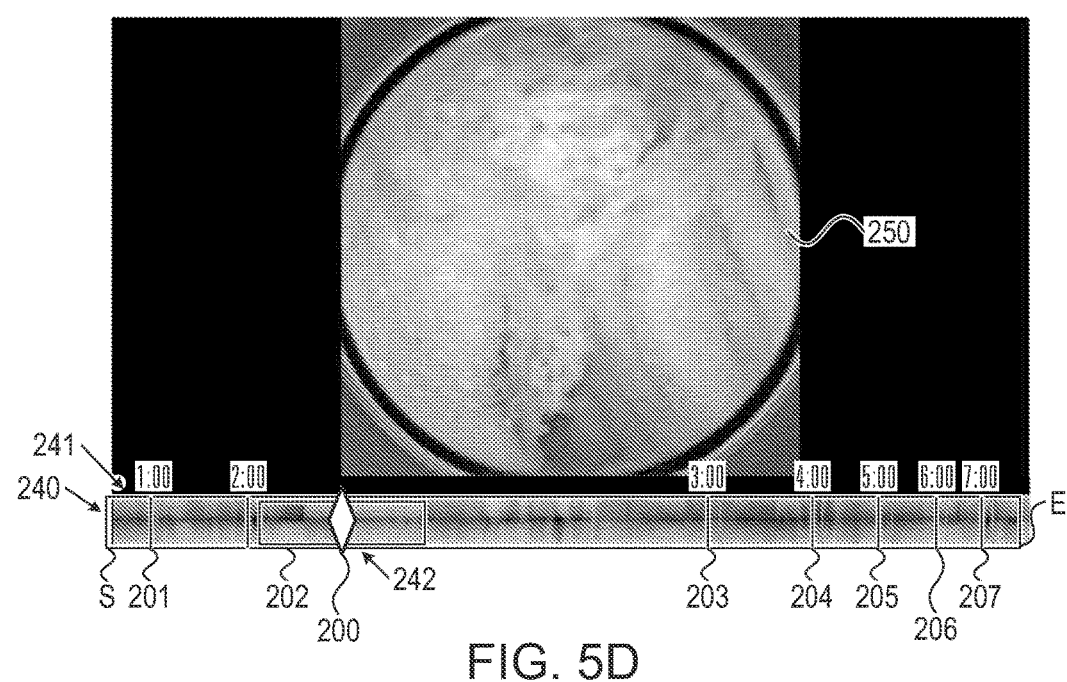

When a user starts playing the image stream, or upon user selection of an image frame or an image stream segment, dynamic preview generator 31 may compute an updated dynamic preview bar, for example continuously while the image stream is streamed or is being displayed in an image stream window (e.g. window 250 of FIG. 5A). In some embodiments, the user may use an input device such as a mouse, touchscreen, or joystick, to select an image stream portion or to hover over an image stream portion, e.g. using the initial preview bar or a dynamic preview bar. Dynamic preview generator 31 may dynamically generate a new (recalculated) dynamic preview bar, which reflects the user's selection or the image stream portion being displayed along the preview bar. The image stream viewing window may automatically display the associated image frames, or may advance or skip to the corresponding portion of the image stream. As the user continues to move the input device along the time line or dynamic preview bar, or as the image stream continues its display and the frames are changing, dynamic preview generator 31 continuously regenerates the dynamic preview bar in order to provide a preview which is correlated with the images simultaneously being selected or displayed. Images which are no longer displayed or which are not adjacent to the concurrently displayed image stream portion, may be summarized in a reduced manner, and a detailed preview may not be provided for them. Continuous or dynamic generation of the dynamic preview bar, in this context, may include constant update, regular update, frequent intermittent update or repeated update of the dynamic preview bar.

Some user interfaces of imaging procedures according to embodiments of the present invention may automatically suggest GI landmarks to the user (e.g. entrance to stomach, entrance to small bowel, entrance to colon). A user may accept the suggestion, or choose another image frame as landmark. When the user clicks on a suggested landmark, the dynamic preview bar may automatically be adjusted or modified to provide a preview of a portion of the image stream in the vicinity of the suggested point in the stream. A detailed preview of frames captured adjacently or within a certain time period as the suggested landmarks is thereby provided to the user, and may enable convenient fine-tuning of the automatically suggested landmark by the user. In other embodiments, if no landmarks are automatically suggested, the user may select a point in the image stream, e.g. by clicking on the summary bar, initial preview bar, or dynamic preview bar, and dynamic preview generator 31 may display the detailed data portion corresponding to the selected point in the image stream. A user may quickly and efficiently fine-tune the landmark selection based on the detailed data provided in the dynamic preview bar for images which are upcoming and/or preceding to the selected point.

In some embodiments, certain segments of a dynamic preview bar may remain fixed, while other portions may be adjusted, modified or recalculated according to the currently viewed image frame(s). For example, if a currently displayed frame corresponds to the third hour of the imaging procedure (out of, e.g., a total procedure time of 8 hours), portions of a dynamic preview bar displayed with, alongside or near the image stream display may be fixed while the portion corresponding to the third hour changes as the movie is played. The dynamic preview and the display need not be contiguous or adjacent to be "along", and in some embodiments are not along or near each other. As an example, portions of the movie corresponding to the first two hours of the imaging procedure may remain fixed, as well as the portions of the movie corresponding to the last 4 hours. The changing portion of the dynamic preview bar may be correlated to visually linked to, or associated with the currently viewed image frames (e.g., of the third hour in this example).

In some embodiments, both summarized image presentation generator 30 and dynamic preview generator 31 may be implemented in one system, e.g. in a single processing unit or using multiple processing units. Summarized image presentation generator 30, dynamic preview generator 31 and other modules or processes discussed herein may be executed by processor 14 or another processor executing software, and thus in some embodiments processor 14 may include summarized image presentation generator 30, dynamic preview generator 31 and/or other components or modules discussed herein. Other methods may be used; for example summarized image presentation generator 30 and/or dynamic preview generator 31 may be dedicated hardware or circuitry.

According to some embodiments, a summarized presentation may be used (e.g. by a processor) for automatic analysis of frame properties, and image stream characteristics. For example, intestinal structures or image segments may be detected or determined in an image frame based on the summarized presentation, and an indication or labeling of image segments, structures, characteristics or event types identified throughout the imaging procedure may be displayed to a user (e.g. by summarized image presentation generator 30, dynamic preview generator 31, and/or processor 14.). Video segmentation may be performed based on the detected motility events. Video segmentation may include, for example, classification of image sequences to a plurality of intestinal event categories.

A summarized presentation may also be used for analysis of motility properties of the image stream. Different motility-related properties may be calculated and summarized, such as pattern, type, rhythm, frequency and/or duration of contractions, average duration of contraction, frequency of contractions in a certain region of the GI tract, etc. Other motility events may be detected and related properties may be calculated and displayed. A range of normal and abnormal values may be presented to the user, for example along with the calculated property, to enable comparison between the normal range and the detected value of the property, and in some embodiments an indication may be provided regarding, for example, abnormal behavior which may have been detected.

Reference is now made to FIG. 2A, which shows exemplary summarized data elements, e.g. strip elements of a summarized presentation bar according to an embodiment of the invention. Summarized data elements 310 and 320 may each include summarized color data from one or more frames of the image stream. Strips 310 and 320 are enlarged in order to demonstrate their structure. A typical size of a strip may be, for example, one pixel in width and a few pixels in length (e.g. 25). Other sizes for strips may be used.

Summarized data elements 310 and 320 may be constructed of a number of pixel portions of different colors, e.g. color portions 311-315 and 321-325 respectively. In some embodiments, the colors may be sorted and arranged in a strip, for example, pixels which have color values which satisfy a certain condition (e.g., a predetermined condition) may be arranged at the top of the strip (e.g. in upper portion 330), and pixels with color values which satisfy a different condition (e.g., a predetermined condition) may be arranged at the bottom of the strip (e.g. lower portion 332).

For example, in vivo images may have a reddish color, typical of the in vivo tissue and/or greenish color, typical of intestinal content. When generating a summarized data element which represents one or more intestinal in vivo image(s), reddish pixels which depict the tissue walls may be arranged, for example, at the bottom portion 332 of the summarized data element. Greenish or yellowish pixels, e.g. due to intestinal content, may be arranged at the top portion 330 of the summarized data element. As a result of such arrangement, images which depict a large amount of intestinal content may have greenish color at the top portion of the strip, and reddish color at the bottom portion of the strip. Images which depict only tissue will have reddish color at the top and bottom portions, and images which depict only intestinal content will have greenish color at the top and bottom portions. Other arrangements are possible, based on pixel values sorted according to sorting parameters.

Sorting parameters may include, for example, as red, green, and blue values (for frames represented in an RGB color space), or hue, saturation, or brightness (e.g. for frames represented in or converted to HSV color space). Any linear or non-linear combination of pixel parameters may be defined as a sorting parameter for arranging the pixels in the strip. A method for sorting and ordering pixels in a summarized data element is further detailed in FIG. 4.

In some embodiments, a middle portion 331 of the strip, e.g. indicated by portions 313 and 323, may include the darkest color(s) found in the one or more image frames. The darkest color may be typical of a lumen hole which may be depicted in the frame(s). If the lumen hole in the frame is relatively large, the corresponding strip (e.g. strip 310) includes a long middle portion 331 with dark color. If the lumen hole is relatively small in the frame (e.g. when a contraction occurs, or when the camera is pointed at a tissue wall), the corresponding strip (e.g. strip 320) includes a smaller middle portion 331 of dark color, or may include substantially no dark color portion.

In some embodiments, a summarized data element may represent a plurality of image frames. The portions of the summarized data element may represent, for example, mean or average colors of portions of the plurality of image frames. For example, the lumen hole size (e.g. measured in pixels) indicated in the summarized data element may be an average of the lumen hole sizes which were calculated per image frame, or a maximum or minimum size, or any other linear combination of the summarized data elements calculated per frame. In other embodiments, the summarized data element generated for a plurality of image frames may be calculated by sorting and sampling pixels amalgamated from the plurality of image frames.

Figure 2B:
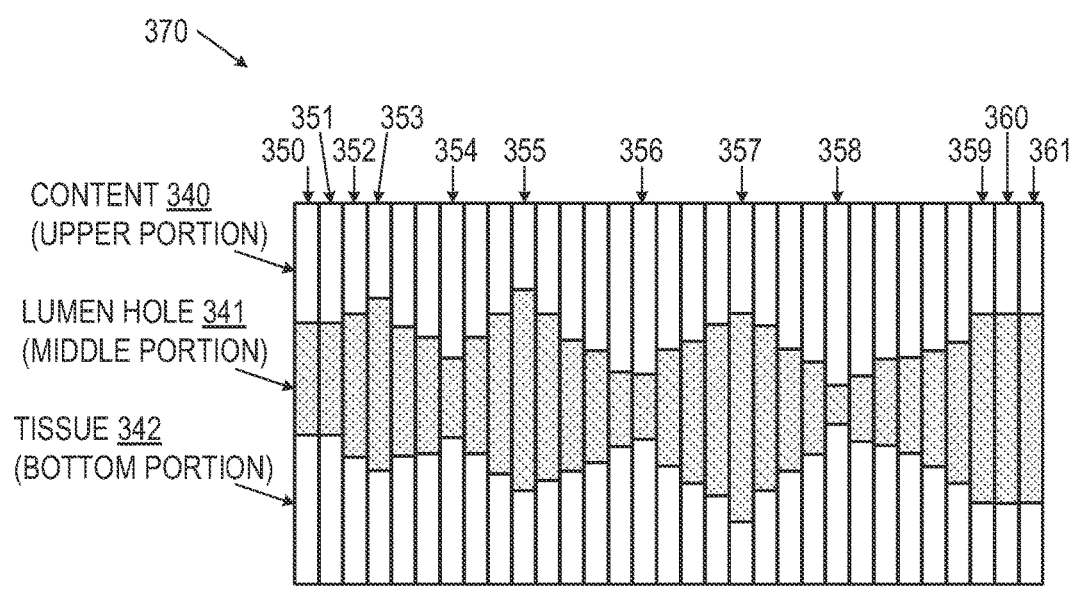
FIG. 2B shows a portion of a summarized image presentation according to an embodiment of the present invention.

A summarized presentation, e.g. bar 370 in FIG. 2B, may include a large number of strips positioned or aligned adjacently, forming a single rectangular bar. The length of the bar may be fixed and predetermined, e.g. according to the amount of display pixels and/or screen space available in the visual display unit. In some embodiments, the length of the displayed summarized presentation may be longer than a single row or column of the visual display unit, and may take up several rows on a computer monitor or screen. In other embodiments, the length of the summarized presentation may be fixed, and the number of image frames represented by a single summarized data element may be calculated, for example, by dividing the number of available pixels in the displayed bar by the number of frames used for generating the bar. In other examples, a summarized presentation may be of a fixed size, and the number of image frames corresponding to a single summarized data element may change, for example dynamically, according to the frame/s being simultaneously displayed in the video display of the image stream (further described in FIG. 7 herein). A video display may include for example a series of still images displayed to produce a moving image.

Each strip may include summarized color data from one or more frames of the image stream. The strips may be updated, for example constantly or continuously updated, while the image stream is played to a user, e.g. as a video stream.

An exemplary summarized presentation bar 370 is illustrated in FIG. 2B. Summarized presentation bar 370 illustrates a plurality of summarized data elements 350-361 which are positioned or aligned adjacent to each other. In this example, each summarized data element is associated with a single image frame. Each summarized data element 350-361 in this example is constructed of three segments: a content segment 340 which appears in the upper portion of each summarized data element, a lumen hole segment 341 which appears in the middle portion of each summarized data element, and a tissue segment 342 which appears in the lower portion. Each summarized data element portion may include several color values, as shown in FIG. 2A.

The summarized presentation bar 370 may provide the user with a summary of the information related to the image frames corresponding to the summarized data elements. For example, a user may note the amount of content (and/or tissue) depicted in the images. The user may also detect variations in lumen hole size in a simple and easy way. For example, summarized data elements 354, 356 and 358 are smaller than other lumen hole segments of summarized data elements 350-361. The image frames corresponding to these elements may be correlated to, for example, a peak of a contraction of the GI organ, since the lumen hole may be smallest during the peak of a contraction. Summarized data elements 353, 355, 357 and 359-361 are larger than other lumen hole segments of summarized data elements 350-361. The image frames corresponding to these elements may be correlated to, for example, an open or relaxed lumen hole.

Patterns of events, e.g. intestinal events may be identified in summarized presentation bar 370, e.g. three contractions may be detected. The first contraction starts at the image frame corresponding to element 353 and ends at the image frame corresponding to image frame 355. A second contraction starts at the image frame corresponding to element 355 and ends at the image frame corresponding to image frame 357, and a third contraction starts at the image frame corresponding to element 357 and ends at the image frame corresponding to image frame 359.

Other types of events, e.g. events related to the GI tract, may be identified based on summarized presentation bar 370, e.g. by a user and/or automatically by a processing unit. For example, a user may be able to differentiate easily between a segment of the image stream which is substantially static or non-informative (e.g. large similarity between sequential images, or large amount of content in the images). When the scene in the image stream changes, or when differences between sequential frames become more detectable, by glancing at the preview bar, the user may be alerted to the changes in advance, and may take action, for example, reduce the viewing speed of the stream, mark the position or time of the change in the image stream (e.g. by generating bookmarks or image thumbnails), add a note or a comment relating to the detected change, etc. In another example, if the user realizes, by analyzing the summarized presentation bar 370, that the upcoming images are not useful or non-informative, he/she may increase the viewing speed.

Figure 3:
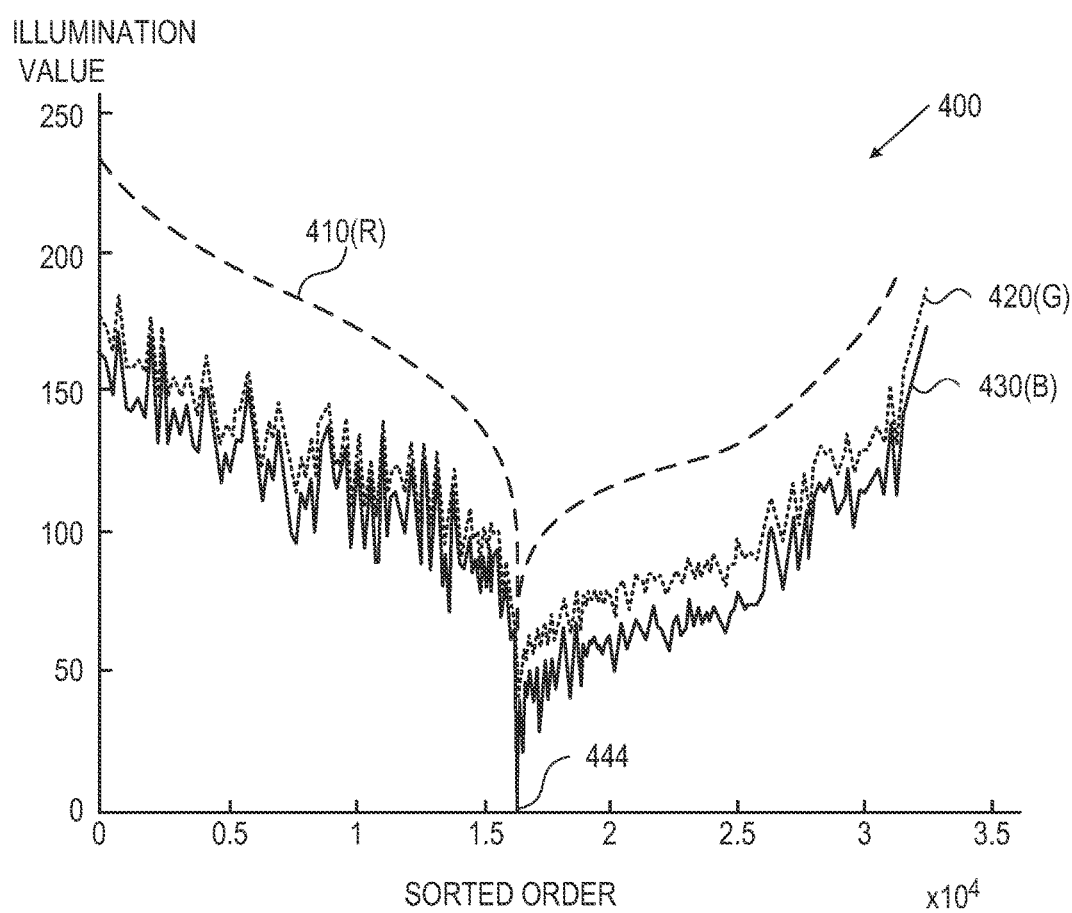
FIG. 3 shows a graph of sorted pixels of an image according to an embodiment of the present invention.

Reference is now made to FIG. 3, which illustrates an example of sorted pixels of one or more image frames, which may be used to generate a summarized data element according to an embodiment of the invention. In this example, the pixel illumination values are presented in an RGB color space, and the pixels are arranged according to the red pixel value. In some embodiments, not all image pixels are sorted; for example, only a selected subset of the pixels from the one or more images may be used, such as a cropped portion of the image(s). The cropped portion may be selected according to the regions of the images which are well-illuminated. This may change from one imaging device to another, based on the illumination distribution of the device, In the present example of graph 400, a subset of $3.5 \times 10^4$ out of $10 \times 10^4$ pixels in an image were sorted. The number of pixels is shown in axis X of graph 400, and the pixel illumination value ranging from 0 to 255 is shown in axis Y.

Line 410 in graph 400 represents values of the red pixels, line 420 represents values of the green pixels, and line 430 represents values of the blue pixels. After sorting the pixels according to chroma-related sorting parameter, the subset of pixels may be divided into two sets, for example by finding the median value of the chroma-related pixel sorting parameter. Point 444 in graph 400 represents the pixel with a median value of the chroma-related pixel sorting parameter, which, in this example, is $$\frac{G}{R}.$$

Other methods may be used to divide the pixels into two sets, for example, average value of the pixels, or a fixed (e.g. predetermined) threshold.

The subset of pixels may be divided into two sets, based on a selected value of the pixels. In one example, the selected value may be a median value of the first sorting parameter, and a first set may include all pixels with $$\frac{G}{R}$$

value below the median (e.g. all values between point (0,0) to point 444). The second set in this example may include all pixels with $$\frac{G}{R}$$

value above the median (e.g. all values with X coordinates larger than point 444 in the graph). Other values may be selected for dividing the pixels into two sets.

After dividing the pixels into two sets, a first set may be arranged in decreasing order according to a first sorting parameter and the second set may be arranged in increasing order according to the second sorting parameter. The sets may be arranged, for example, in two lists, arrays or other data structures which allow ordering. The second sorting parameter may be luminance-related, e.g. based on the brightness of the pixel. For example, the luminance-related sorting parameter may be the red value of pixels in the RGB color space. The red value of in vivo images may be highly correlated to the pixel brightness. In another embodiment, the pixels may be transformed to HSV color space, H (hue value, dominant wavelength) may be used as the first sorting parameter, and the V value (e.g. brightness value) of the pixel may be used as a second sorting parameter. Other numbers of sorting parameters may be used.

The two ordered lists may be combined or appended into a single list as shown in graph 400. Other methods and other pixel sorting parameters may be used to sort the pixels and divide them into two (or more) sets. The arranged lists, which were combined into a single list, may be used to generate a summarized data element.

Figure 4:
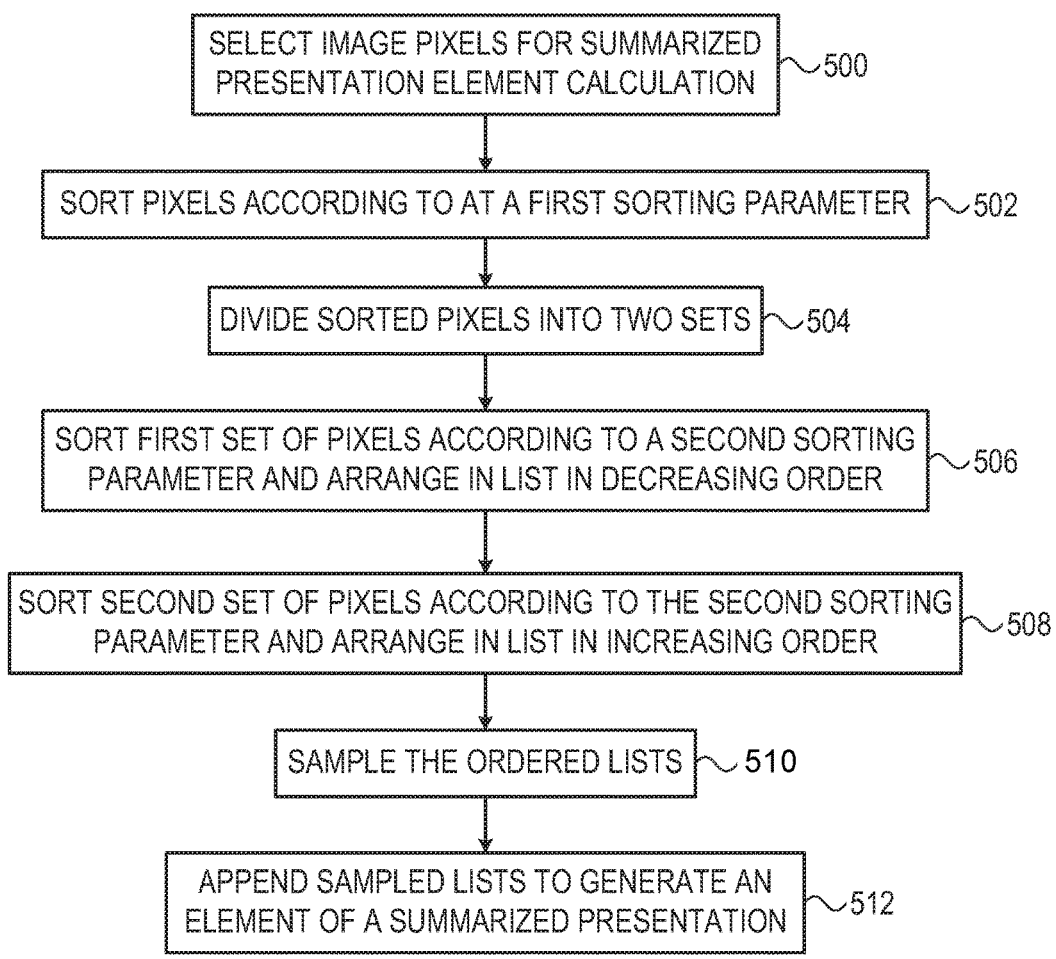
FIG. 4 illustrates a flow chart of a method for generating a summarized image element according to embodiments of the present invention.

Reference is now made to FIG. 4, which is a flow chart of a method for generating a summarized presentation element according to an embodiment of the invention. One or more image frames may be received, for example by a processor or computation unit such as summarized image presentation generator 30. The image frame(s) may be represented in RGB color space and may include R, G and B values per pixel. In operation 500, a subset of pixels may be selected from each image frame(s). The subset of pixels may include, for example, pixels within a certain predetermined region of each image (e.g. pixels in a central round or square region of a predetermined size and position in the image frame). In some embodiments, the subset of pixels may be selected such that the pixels satisfy a certain mathematical condition. In some embodiments, all pixels of an image frame may be used.

In operation 502, the pixels may be sorted according to a first sorting parameter. In one embodiment, a first sorting parameter may be chroma-related, and may reflect perceived intensity of a pixel color. Examples of a first sorting parameter include: R, G or B value of the pixel, or a linear or nonlinear combination of these values e.g.

$$\frac{G}{R}$$

(in the RGB color space). The pixels may also be converted to different color spaces, such as HSV, and any linear or non-linear combination of pixel values in the initial color space or in the new color space may be used as a sorting parameter. Another example of chroma-related sorting parameter is the H (hue) value of pixels in an HSV color space.

Other sorting parameters may be used. For example, different image processing detectors may be activated, and detector scores may be obtained per pixel in the image (or in a plurality of images). In one embodiment, a first sorting parameter may be content detection score of a pixel. An exemplary content detector which may be used to obtain content detection score per pixel is disclosed in U.S. Pat. No. 7,567,692 to Buzaglo et al, and in U.S. patent application Ser. No. 13/729,263 To Peleg, both of which are assigned to the common assignee of the present invention and incorporated by reference herein. Other methods may be used to obtain content detection scores per pixel.

In operation 504 the sorted pixels may be divided into two sets. The division into two sets may be performed, for example, by calculating a median or mean value of the pixels' first sorting parameter value. E.g., a first pixel set may include the pixels with sorting parameter value lower than the median, and a second pixel set may include the pixels with sorting parameter value which are higher than the median. Other methods may be used to divide the sorted pixels into two sets. For example, a predetermined or fixed value of the first sorting parameter may be used as a threshold, and all pixel values above the threshold may be assigned to a first set, and the rest of the pixels may be assigned to the second set.

In operations 506 and 508, each pixel set may be sorted according to a second sorting parameter. The second sorting parameter may include, for example, any linear or non-linear combination of pixel values, such as R, G and B (in an RGB color space). The exemplary sorting parameter shown in graph 400 is R (red value). The pixels may also be converted to different color spaces, such as HSV, and any linear or non-linear combination of pixel values in the new color space may be used as a second sorting parameter. Image pixels from one color space to another, e.g. from RGB color space to HSV color space, and the V value of each pixel represented in the HSV color space may be used for sorting each pixel set. A first set, for example the lower set, may be sorted according to the second sorting parameter and the pixels may be arranged in a list in descending order. The second set may be sorted according to the second sorting parameter and the pixels may be in a list in ascending order. When sorting one set in a decreasing order and the other set in an increasing order, the resulting arrangement may create a middle portion which is darker in the summarized data element, and may indicate the appearance and/or size of the lumen hole in the represented image frame(s).

In some embodiments, the second sorting parameter may be based on a lumen detector score. A lumen detector may include image processing functionality which may provide a lumen score, for example per pixel of an image frame. The lumen score may indicate the probability of the pixel depicting a lumen hole in the image. Lumen detection may be performed, for example, based on pixel illumination parameters, and/or on edge detection of shape recognition methods in the image. Exemplary methods of detecting lumen hole (e.g. lumen blob) which may be used are disclosed in US Patent Application Publication 20110044515 to Spyridonos et al. In this example, the first sorting parameter may be according to a content score of the pixels. After assigning the content score (e.g. in operation 502), the pixels may be divided into two sets based on the median or mean content score, and the pixels may be sorted according to the lumen score.

In operation 510 the ordered lists may be sampled. For example, the number of pixels in the ordered lists may be 35,000, while the number of pixels which are selected for the summarized data element may be in the range of, for example, 20 to 50 pixels. Therefore the sampling scheme may need to reduce the number of pixels considerably. An example sampling scheme may include selecting pixels from the sorted lists by using a fixed interval, for example, one pixel out of every 200 pixels in the sorted list may be selected. The selected pixel may satisfy a certain condition, e.g. the pixel with the highest value (of the sorting parameter, or another selected value) in the interval. In another example every Nth pixel may be selected (e.g arbitrarily).

In yet another example, the sampling scheme may be defined such that the summarized data element will include several different portions, each portion representing a certain characteristic of the frame. The sorted pixels may be selected such that a number of detectable portions, for example, three detectable portions are created, e.g. as shown in FIG. 2A, a top, middle and bottom structure of the summarized data element which may represent intestinal content pixels (upper portion in FIG. 2A), the lumen hole (middle portion in FIG. 2A) and tissue pixels (bottom portion in FIG. 2A). In order to enhance the differences between the portions and create an informative summarized presentation, the sampling scheme may be nonlinear, and more pixels from one portion may be selected than pixels from the other portions. In one embodiment, more pixels may be selected (sampled) from the darker portion, e.g. the middle portion including darker pixels representing the lumen hole. For example, referring to graph 400 in FIG. 3, more pixels may be sampled from the area around point 444 which corresponds to the darker pixels in the image that represent the lumen hole. Such sampling scheme may emphasize or highlight image frame properties and/or intestinal contractions or other events which may be detected based on the size of the lumen hole in the image. Pixels from other areas of the graph may be sampled less densely. If lumen detection was performed on the image frame (e.g. to determine a lumen score per pixel), the area of the lumen hole may be calculated (e.g. by determining the number of pixels in the lumen hole). Similarly, if content detection was performed, the area containing content (or clear tissue) in the image may be calculated. Each region (content, lumen and tissue) of the image frame may be sampled and the pixels representing each region may be selected to generate the summarized data element.

After sampling the pixel sets, the sampled pixels may be combined or appended to generate a summarized data element, e.g., a strip, representing the image frame (operation 512). In some embodiments, if the summarized data element is calculated for a plurality of image frames, a summarized data element may be generated per image of the plurality of images, then an average of the summarized data elements may be calculated (e.g. average per portion of a summarized data element). In other embodiments, a summarized data element for multiple images may be calculated by sorting pixels from the multiple images, and ordering and sampling them as described above. Other methods of creating a summarized data element from multiple frames may be used.

Multiple generated summarized data elements (e.g. pixel strips) may be combined, for example by positioning or aligning the summarized data elements adjacently in the form of a rectangle or bar to create a summarized presentation. The generated summarized presentation may be in the form of a fixed (or static) bar such as summarized presentation bar 370 in FIG. 2B, or in the form of a dynamic bar e.g. dynamic preview bar 240 of FIGS. 5A-5D.

A dynamic preview bar may be generated based on summarized data elements, for example by positioning the summarized data elements adjacently to each other, e.g. in a longitudinal preview bar or window shown for example in FIGS. 5A-5D. In some embodiments, the dynamic preview bar may be generated by zooming-in on a portion of a fixed or constant preview bar, where the zoomed-in or enlarged portion of the preview bar is associated with the portion of the image stream which may simultaneously be displayed in an image stream viewing window.

The process of reviewing an image stream captured by a capsule may take a relatively long time for a professional reviewer (e.g. a physician or nurse). Displaying a detailed preview of upcoming portions of the image stream may assist in reducing the review time. In one embodiment, a detailed preview of images may be provided, for example along the image stream viewing window. A reviewing physician may accelerate the viewing rate of the image stream when the upcoming images are mostly static, non-changing or non-informative. E.g., for portions of the image stream which depict images which are repeated or highly similar, or for portions of the stream which depict mostly turbid content, a reviewer may glance at the dynamic preview bar, and analyze whether the upcoming images are interesting or informative. Similarly, the reviewer may become more alert, or reduce the viewing rate, when the dynamic preview bar indicates that upcoming frames are highly dissimilar, changing at a fast rate, or if an interesting intestinal event may be determined from the dynamic preview bar. Such acceleration or deceleration of the viewing rate may reduce viewing time, and/or may improve the review process, e.g. increase the efficiency, quality or sensitivity of the review.

A dynamic preview bar may also be used for other purposes. In one example, a physician reviewing the movie stream may want to determine GI landmarks or organs (e.g. entrance to small bowel, colon, etc.). The reviewer may, for example, move an input device such as a mouse over a dynamic preview bar, and a detailed preview may be displayed for the portion of the image stream which corresponds to the segment of the preview bar which is indicated by the input device. The physician may thus be able to determine the desired landmark quickly and efficiently.

Reference is now made to FIGS. 5A-5D, which include an exemplary display of an image stream and a dynamic preview bar according to an embodiment of the invention. FIGS. 5A-5D each include a current frame of an image stream displayed in window 250, simultaneously displayed alongside or near a dynamic preview bar 240 which is calculated for the current frame. The image stream frames and preview bar 240 need not be displayed next to each other, but may be alongside each other and separated from each other and need not be near each other. The reference numerals which appear in FIGS. 5A-5D are repeated among the figures to indicate corresponding elements throughout the serial views. Cursor 200 (indicated by a dashed line), specifies the position of the currently displayed image frame in the complete set of captured frames of the image stream, chronologically ordered according to time of capture. A time of capture of the frame may be defined, for example, as the time elapsed from between the beginning of the procedure until the current frame was captured; other measures of time of capture may be used. Time indications 241 indicates the time (e.g. in hours) along dynamic preview bar 240, e.g. corresponding to lines 201-207. The time indications 241 may be marked in different positions or intervals along dynamic preview bar 240, according to the frame currently displayed in window 250.

Points S and E in the dynamic preview bar indicate, respectively, the start and end of the imaging procedure. These points may be fixed in the dynamic bar presentation, e.g. indicated at the same position for every displayed image frame in window 250. For example, dynamic preview bar 240 may be displayed simultaneously along the display of the image stream as a bar of a fixed, predetermined size. The fixed size of dynamic preview bar 240 may change from one computer display to another, e.g. according to the available size or resolution of monitor 18 and/or the application window viewed by the reviewer. For example, dynamic preview bar 240 may be of 200 pixels in length and 20 pixels in height.

Cursor 200 indicates a summarized pixel data strip corresponding to the currently displayed image. Cursor 200 may be positioned along dynamic preview bar 240, in the relative position between points S to E, according to the capture time or another order measure of a currently displayed frame (or a plurality of frames). Exemplary methods of displaying a plurality of frames in a single time slot are disclosed in U.S. Pat. No. 7,505,062 to Davidson et al., incorporated by reference herein in its entirety. For example, cursor 200 may be positioned between points S to E, in a point which corresponds to the ratio between the time which passed from the beginning of the procedure to the time of capture of the currently displayed image. For example, when the cursor is situated exactly at half the distance between points S to E, it indicates that the currently displayed image was captured after half the duration of the imaging procedure.

In some embodiments, in order to provide more detailed data corresponding to images captured in proximity to near the currently displayed image, time line indications 241 reflecting the capture time of images (e.g. time that passed since the beginning of the imaging procedure) may be distorted, e.g. equal time intervals marked on the dynamic preview bar 240 (e.g. 1 hour) may not be distributed evenly in fixed distances, and may change dynamically in accordance with the position of cursor 200 and the currently displayed frames. Cursor 200 may be positioned at any point on the timeline, and may indicate a ratio or proportion between time that passed from the beginning of the imaging procedure to the currently displayed image, and the total amount of time that the procedure lasted. It is noted that although the time scale is distorted, the position of cursor 200 along preview bar 240 may accurately reflect said ratio. The distribution of frames according to their time of capture and corresponding to the simultaneously displayed frame is further described with relation to FIGS. 6A and 6B herein.

Lines 201-207 may indicate fixed time intervals of frame capture time. Frame capture time may be for example absolute time (the time of day the frame was captured), time relative to a start of image capture, or some other time measure. For example, if the procedure displayed in FIGS. 5A-5D lasted a total of 8 hours, each line may indicate one hour. Other time intervals may be used. As can be seen in the series of FIGS. 5A-5D, in each figure, lines 201-207 may be situated in different positions along dynamic preview bar 240, according to the capture time of the currently displayed image in window 250. FIGS. 5A-5D show four images captured in ascending times of capture throughout a single imaging procedure. The images in FIGS. 5A and 5B were captured between the first hour (indicated by line 201) and the second hour (indicated by line 202), while the images in FIGS. 5C and 5D were captured between the second hour and the third hour (indicated by line 203) of the procedure.

It may be observed that dynamic preview bar 240 includes portions which are very similar throughout all four FIGS. 5A-5D, for example the portion of dynamic preview bar 240 that is positioned between point S to line 201, and the portion between line 203 to line E. The portions which change the most are those associated with the presently displayed image in window 250, which are situated, in this example, between lines 201 to 203. These portions are modified to reflect pixel characteristics of the currently and/or recently displayed image frame(s), and may provide a detailed preview of upcoming frames in the image stream. A preview window 242, which may or may not be marked or visually emphasized along preview bar 240, may indicate the portion of preview bar 240 which is most detailed or zoomed-in. In some embodiments, the most detailed preview portion of dynamic preview bar 240 may be provided both for upcoming images as well as for recently-viewed images. Portions of dynamic preview bar 240 situated just before cursor 200 and just after cursor 200 may provide the most detailed information to the viewer, while the rest of the dynamic preview bar 240 may provide less detailed information, or information in lower resolution. Such continuously updated computation of dynamic preview bar 240 may allow detecting different frame characteristics and/or motility-related events in the image stream, and may allow the reviewing physician to be more alert to upcoming changes in the image stream, for example when reviewing a substantially static or non-informative portion of the image stream.

Reference is now made to FIG. 6A, which illustrates an example of time distortion of preview bar elements (representing image frames) positioned on the dynamic preview bar according to an embodiment of the invention. The example reflects the time distortion function applied to or correlating to the position on the preview bar of a dynamic preview bar element representing one or more specific image frames being displayed in an image stream viewing window (or a preview bar element being selected, e.g. using an input device). The dynamic preview bar in this example includes approximately 510 pixels in length, shown in X axis of graph 440. Other lengths may be used. The amount of images in the image stream is approximately 56,000, as indicated by Frame Identification ("Frame ID") in Y axis of graph 440. Curve 450 correlates a Frame ID (which is, for example, a sequential number of the frame captured since the beginning of the imaging procedure) to a position in the generated dynamic preview bar. Point 452 in the graph corresponds to the current frame being displayed in an image stream viewing window, which in this example corresponds to Frame ID 150,000.

The function shown in graph 440 may be piecewise linear or nonlinear. In this example, the function is non-linear, and may be divided into three sections: a first section from point (0,0) in the graph to point 451, a second section from point 451 to 453, and a third section from point 453 to 455. The slope of the curve may change substantially between these sections—in the first section the slope is quite steep and gradually becomes less steep as it nears point 451, in the second section the curve 450 is substantially linear with almost zero inclination (almost horizontal), and in the third section the slope starts near horizontal and gradually grows steeper towards point 455. The number of image frames corresponding to the first section is approximately 16,000, which are represented by approximately 100 strips of pixels (in the dynamic preview bar). In the second section each frame corresponds to a single pixel strip in the dynamic preview bar, in other words, a bar of 100 pixels in length represents 100 images. The second section corresponds to the detailed portion of the dynamic preview bar, which provides the most detailed information correlating to the image frames associated with the second section of the curve. The number of image frames corresponding to the third section (between point 453 to 455) is approximately 40,000, and these frames are associated with the last portion of the dynamic preview bar which includes the remaining pixel strips (approximately 310 in this example). Other numbers of strips and frames may be used. In this example, the first and third sections of the curve are associated with the reduced data portions of the dynamic preview bar. It is noted that the time distortion in these section is not linear, and changes within each section, such that the most reduced data is associated with the edges or ends of the image stream (e.g. beginning and end of the stream), and as the frame ID gets nearer to the current fame being displayed, the data is more detailed.

In other embodiments, the function may be piecewise linear, and may be divided similarly into three sections, the first with a predetermined steep slope, corresponding to earlier viewed images in the image stream, the second with a nearly horizontal slope (corresponding to the preview window e.g. window 242 of the preview bar), and the third with a predetermined steep slope, corresponding to images which have not yet been displayed in the image stream, and which are not imminent to the currently displayed image frame.

These examples demonstrate a time distortion of preview bar elements positioned on the dynamic preview bar, in order to provide more detailed data for image frames adjacent to the currently displayed frame, and less data for distant frames. The time distortion function may be adjusted, for example per every displayed frame or every predetermined time period. As the displayed image stream is reviewed, the current Frame ID progresses, and the time distortion function may be constantly recalculated or updated in order to provide more detailed pixel and frame information correlating to the presently displayed frame and to a limited number of frames adjacent to it (e.g. one pixel strip represents one frame for a sequence of 100 frames), and less detailed information for frames which are distant from the presently displayed frame (where one pixel strip may represent, e.g., 50 or 100 frames). In some embodiments, curve 450 may comprise more than three sections, and different time distortion functions may be applied per section.

Reference is now made to FIG. 6B, which illustrates various time distortion functions, each correlating to an image frame captured in a different time. The reference numerals are repeated among FIGS. 6A and 6B to indicate corresponding elements. Three dynamic preview bars may be generated according to time distortion functions represented by curves 450, 460 and 470. All the dynamic preview bars are generated for the same image stream, and the variation is due to the current image frame being displayed. The dynamic preview bar generated in this example includes approximately 510 pixels in length, shown in the X axis, "Location on Dynamic Preview Bar", of graph 441 (other lengths may be used), and the amount of images in the image stream which is represented by the dynamic preview bar is approximately 56,000, as indicated by Frame Identification ("ID") in Y axis of graph 441. Curves 450, 460 and 470 each correlate a Frame ID to a position of the corresponding preview bar element in a generated dynamic preview bar. Point 452 on curve 450 corresponds to a point in time during a review of the image stream, in which a frame being displayed in an image stream viewing window, corresponds, in this example, to Frame ID 150,000. Point 462 on curve 460 corresponds to a different point in time during review of the same image stream, the frame being displayed in an image stream viewing window corresponding to Frame ID 230,000. Point 472 on curve 470 corresponds to yet another point in time during review of the same image stream, the frame being displayed in an image stream viewing window corresponding to Frame ID 380,000. In some embodiments, the correlation of frame to position on the dynamic preview bar may be calculated based on frame capture time instead of Frame ID.

It is noted that all the points representing the current frame being displayed at various points in time (e.g. points 452, 462, 472) are positioned on a straight line 480. This reflects the linear advancement of the cursor (e.g. cursor 200) positioned on the dynamic preview bar at the point which corresponds to the time of capture of the image being displayed, regardless of the time distortion function which determines the position of the other preview bar elements representing images on the dynamic preview bar.

The segment of curve 450 positioned between points 451 to 453 correlates to the most detailed data segment of the dynamic preview bar displayed while frame ID 150,000 is being displayed. Similarly, the segment of curve 460 positioned between points 461 to 463 correlates to the most detailed data segment of the dynamic preview bar displayed while frame ID 230,000 is being displayed, and the segment of curve 470 positioned between points 471 to 473 correlates to the most detailed data segment of the dynamic preview bar displayed while frame ID 380,000 is being displayed.

Figure 7:
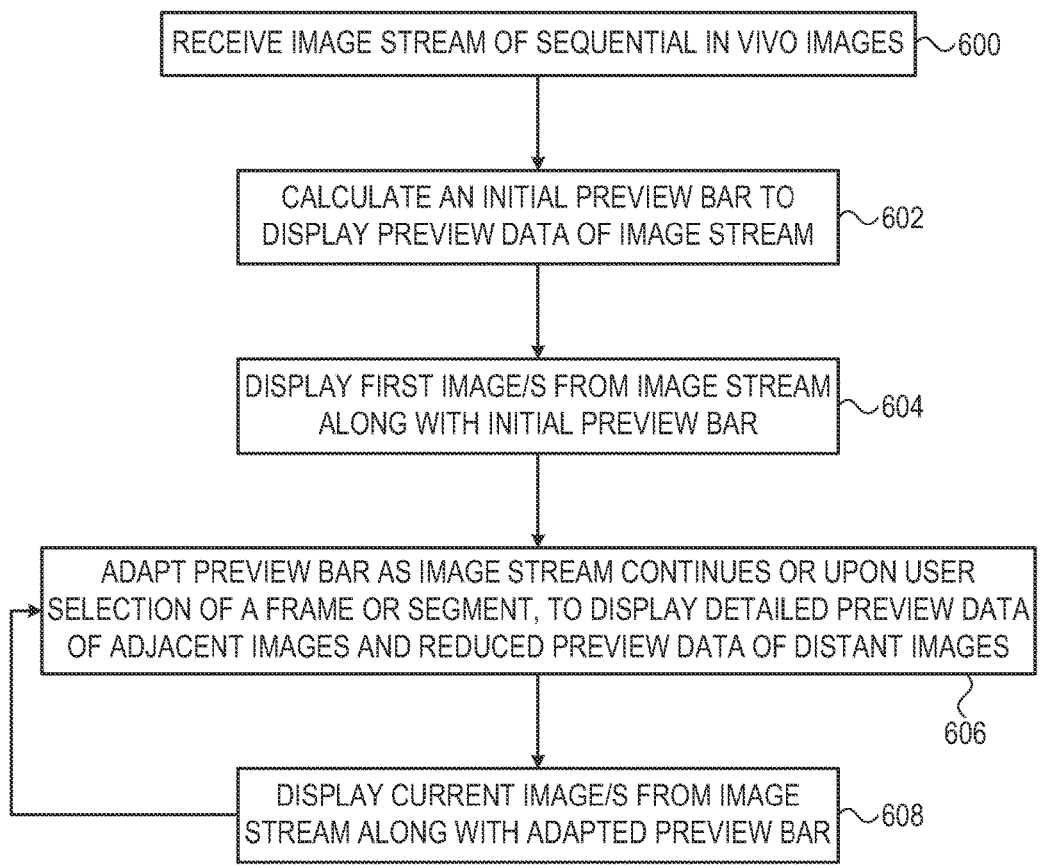
FIG. 7 is a flow chart of a method for displaying a dynamic preview bar according to embodiments of the present invention.

Reference is now made to FIG. 7, which is a flow chart of a method for displaying a dynamic preview bar according to an embodiment of the invention. In operation 600, a stream of images may be received and stored, for example by an image receiver such as receiver 12. The stream may include a plurality of images captured sequentially, for example by a video camera or by an in vivo imaging device, and each image may have a sequential number and/or may be associated with a time of capture.

In operation 602, an initial preview bar may be computed for the image stream. The initial preview bar may be comprised of preview bar elements, e.g. summarized data elements 310 and 320, and each element may be calculated for one or more image frames. In some embodiments, the preview bar elements of the initial preview bar may be calculated in other methods, for example by calculating an average of the colors of an image frame. In the initial state, the preview bar may be generated with no time distortion between represented image frames, e.g. each preview bar element may represent the same amount of frames from the image stream. The initial preview bar may be fixed or static. In other embodiments, the initial preview bar may be generated such that detailed preview data is generated for a group of first frames of the image stream (e.g. for the first frame and for a certain number of adjacent frames), and reduced preview data is generated for the rest of the frames. In this embodiment, the first portion of the preview bar may display detailed preview information to a user, who may use this information to detect image properties such as: luminance parameters, color or chroma parameters, lumen hole size, appearance, position and variation of the image properties, or scene changes along the detailed preview portion. The user may also detect turbid content level of the frames associated with the detailed portion of the dynamic preview bar. In some embodiments, the detection of these properties may be performed automatically (e.g. by processing unit such as processor 14), and the detected properties or changes in the image stream may be displayed to the user. In one example, changes of scenes may be detected in the image stream by analyzing the detailed portion of the dynamic preview bar, and an indication of the changes may be displayed to a user, for example as marks or indications on the dynamic preview bar, or along the image stream.

In operation 604, the first image (or multiple images) from the stream may be displayed to a user, for example alongside the initial preview bar. When the image stream starts playing, e.g. when a user presses the "play" button on a User Interface associated with the streaming display, the initial preview bar may be replaced with a dynamic preview bar as described herein.

In operation 606, a dynamic preview bar may be computed for an image (or a plurality of images) which may be simultaneously, substantially simultaneously or concurrently displayed from the image stream. In another option, the user may select a point or segment on the dynamic preview bar, or on the initial preview bar, e.g. using an input device such as a mouse, and a new dynamic preview bar may be computed and displayed for the selected portion of the image stream. The dynamic preview bar may be generated such that detailed preview data is calculated corresponding to images adjacent to the concurrently displayed images, and reduced preview data is calculated corresponding to distant images. The generation of preview bar elements may include, for example, operations listed in FIG. 4 herein. In some embodiments, other methods of generating a preview bar or a summarized graphical presentation of images may be used, e.g methods disclosed in U.S. Pat. No. 7,215,338 to Horn et al., and/or US Patent Application Publication Number 20070060798 to Horn et al. Generating detailed preview data may include generating summarized pixel data corresponding to a single frame, e.g. a preview bar element in the form of a pixel strip. The detailed preview data may be generated for a currently displayed image frame(s) which is viewed by a reviewer of the imaging procedure, and for image frames which are located adjacent to the current frame. In one embodiment, detailed preview data may be computed for the current image(s) being displayed, and for a predetermined number (e.g. 50) of previous images and/or upcoming images in the image stream, or for images captured a predetermined time period before and/or after the currently displayed image(s).

Reduced preview data may be generated for images which are positioned further from the currently displayed image, e.g. images which are positioned a distance of over a predetermined number of images from the present frame in the sequential image stream (or images captured more than a predetermined or computed time period before or after the currently displayed frame). In one embodiment, the reduced preview data may include a plurality of preview bar elements (e.g. pixels strips), each preview bar element summarizing pixel data corresponding to multiple sequential images from the image stream. In some embodiments, there may be different degrees of reduced preview data, and there may be gradual reduction of the level of detail displayed in a preview bar for frames that are distant from the currently displayed frame(s), e.g. according to the distance of the frame from the current frame. In other embodiments, a preview window (e.g. preview window 242) may present the detailed preview data for a portion of the image stream, while the rest of the preview bar may present reduced preview data for the images not associated with the preview window portion of the dynamic preview bar.

In operation 608, one or more frames of the image stream may be displayed, for example along with the dynamic preview bar generated for the currently displayed frame/s. The dynamic preview bar may be positioned in various positions on the display. In some embodiments, the image stream and the dynamic preview bar may be displayed simultaneously on separate monitors or displays. User input may be obtained, for example, a user may select or click a certain point on the dynamic preview bar in order to display the segment or portion of the image stream which is associated with the selected point of time which was clicked.

Operations 606-608 may be repeated, looped or iterated, for example intermittently, e.g. in fixed or varying time intervals or after every predetermined number of frames being displayed. Operations 606-608 may be repeated, for example continuously or substantially continuously throughout the duration of the image steam review, such that the dynamic preview bar is repeatedly recalculated and adapted to the current image frame displayed in the video stream window.

It is noted that the image stream need not necessarily be a stream of in vivo images. Reduced and dynamic preview data may be generated for any other type of images, for example, movies, image streams captured by security or surveillance cameras, etc.

Other operations or series of operations may be used.

Different embodiments are disclosed herein. Features of certain embodiments may be combined with features of other embodiments; thus certain embodiments may be combinations of features of multiple embodiments.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A computer-implemented method for displaying an image stream captured by an in vivo imaging device, the method comprising:
    receiving an image stream captured by the in vivo device, the image stream comprising a plurality of image frames, each image frame comprising a plurality of pixels;
    automatically generating a dynamic preview bar, wherein said dynamic preview bar comprises:
    a series of adjacent data elements;
    a detailed data segment comprising an adjacent series of data elements of the series of adjacent data elements, each data element in the detailed data segment providing data which represents one or more image frames from a first portion of the image stream;
a reduced data segment comprising an adjacent series of data elements of the series of adjacent data elements, each data element in the reduced data segment providing data which represents a plurality of image frames from a second portion of the image stream, wherein the number of image frames corresponding to a data element of the reduced data segment is greater than the number of image frames corresponding to a data element of the detailed data segment, and wherein said detailed data segment is generated for each of the at least one image frames being displayed in each time slot in the video display; and
displaying, on the visual display, the dynamic preview bar along the video display of the image stream, wherein the display of the dynamic preview bar is continuously updated by displaying in each time slot the detailed data segment generated for the at least one image frame currently being displayed in the video display.

2. The method of claim 1 wherein the detailed data segment is generated for a sequence of image frames adjacent to the at least one frame currently being displayed in the video display.

3. The method of claim 1 wherein the detailed data segment is generated for segments of the image stream which are selected by a user, and wherein adjacent data elements of the detailed data segment correspond to sequential images from the image stream.

4. The method of claim 1 wherein the reduced data segment is generated for image frames which are not adjacent to the frame currently displayed in the video display.

5. The method of claim 1 wherein the detailed data segment is visually emphasized on the visual display unit.

6. A system for displaying an image stream captured by an in vivo imaging device, the system comprising:
a processor to:
receive an image stream captured by the in vivo device, the image stream comprising a plurality of image frames, each image frame comprising a plurality of pixels; and
generate a dynamic preview bar, wherein said dynamic preview bar comprises:
a series of adjacent data elements;
a detailed data segment comprising an adjacent series of data elements of the series of adjacent data elements, each data element in the detailed data segment providing data which represents one or more image frames from a first portion of the image stream; and
a reduced data segment comprising an adjacent series of data elements of the series of adjacent data elements, each data element in the reduced data segment providing data which represents a plurality of image frames from a second portion of the image stream, wherein the number of image frames corresponding to a data element of the reduced data segment is greater than the number of image frames corresponding to a data element of the detailed data segment, and wherein said detailed data segment is generated for each of the at least one image frames currently displayed in the video display; and
a visual display unit to display a video display of the image stream, wherein at least one image frame is displayed in each time slot, and the image frames are displayed sequentially according to their frame capture time, the visual display unit further to display the dynamic preview bar along the video display of the image stream, and
wherein the detailed data segment is continuously updated according to each of the the at least one image frame being displayed in the video display.

7. The system of claim 6 wherein the processor is to generate the detailed data segment for a sequence of image frames adjacent to the at least one image frame currently being displayed in the video display.

8. The computer-implemented method for displaying an image stream captured by an in vivo imaging device of claim 1, wherein the data elements in the detailed data segment and the data elements in the reduced data segment are generated for at least a subset of the image frames, each data element in the detailed data segment and the data elements in the reduced data segment corresponding to at least one image frame from the subset of the image frames, wherein generating a data element in the detailed data segment and the data elements in the reduced data segment comprises:
ordering pixels of one or more image frames according to a first sorting parameter;
sampling the ordered pixels according to a predetermined sampling scheme to acquire a sampled set of ordered pixels; and
combining pixels of the sampled set of ordered pixels to form a data element.

9. The method of claim 8 wherein generating a data element in the detailed data segment and the data elements in the reduced data segment comprises selecting a subset of pixels from each of the one or more image frames according to a predetermined condition, and wherein ordering pixels comprises ordering the subset of pixels.

10. The method of claim 8 wherein said first sorting parameter is based on detecting a lumen hole in the image frames.

11. The method of claim 8 wherein pixels are represented in R,G,B (Red, Green, Blue) color space, and the first sorting parameter is computed based on a combination of R, G, and/or B values.

12. The method of claim 8 wherein generating a data element comprises re-ordering pixels of one or more image frames according to a second sorting parameter.

13. The method of claim 12 comprising:
dividing the sorted pixels into two sets based on the first sorting parameter,
arranging the first set in decreasing order according to the second sorting parameter, and
arranging the second set in increasing order according to the second sorting parameter.

14. The method of claim 8 wherein each data element in the detailed data segment and the data elements in the reduced data segment is a line of pixels.

15. The method of claim 8, wherein the subset of frames includes a sequence of consecutive image frames from the image stream.

16. The method of claim 8, comprising determining image properties or intestinal events based on the dynamic preview bar.

17. The system for displaying an image stream captured by an in vivo imaging device of claim 6, wherein the dynamic preview bar comprises data elements, and wherein the data elements are generated for at least a subset of the image frames, each data element corresponding to the at least one image frame from the image stream, wherein generating a data element comprises:

ordering pixels of one or more image frames according to a first sorting parameter;

sampling the ordered pixels according to a predetermined sampling scheme to acquire a subset of ordered pixels; and combining pixels of the subset of ordered pixels to form a data element.

18. The system of claim 6 wherein each data element in the detailed data segment and the data elements in the reduced data segment comprises a line of pixels.

19. The system of claim 6, wherein each data element in the detailed data segment and each data element in the reduced data segment provides data representing a sequence of consecutive image frames from the image stream.

20. The method of claim 1, wherein each data element in the detailed data segment and each data elements in the reduced data segment summarizes information related to its corresponding one or more image frames.

21. The method of claim 1, wherein updating the detailed data segment is automatic.

22. The system of claim 6, wherein updating the detailed data segment is automatic.

23. The method of claim 1, wherein the series of adjacent data elements comprises image frame pixels.

24. The system of claim 6, wherein the series of adjacent data elements comprises image frame pixels.

* * * * *